United States Patent
Goto et al.

(10) Patent No.: US 9,594,135 B2
(45) Date of Patent: Mar. 14, 2017

(54) MAGNETIC RESONANCE IMAGING APPARATUS AND METHOD FOR ADJUSTING EXCITATION REGION

(75) Inventors: Tomohiro Goto, Tokyo (JP); Takashi Nishihara, Tokyo (JP); Hiroyuki Itagaki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 1039 days.

(21) Appl. No.: 13/496,921

(22) PCT Filed: Sep. 22, 2010

(86) PCT No.: PCT/JP2010/066346
§ 371 (c)(1),
(2), (4) Date: Mar. 19, 2012

(87) PCT Pub. No.: WO2011/040289
PCT Pub. Date: Apr. 7, 2011

(65) Prior Publication Data
US 2012/0194190 A1 Aug. 2, 2012

(30) Foreign Application Priority Data

Sep. 29, 2009 (JP) ................................ 2009-224662

(51) Int. Cl.
*G01R 33/48* (2006.01)
*G01R 33/483* (2006.01)
(Continued)

(52) U.S. Cl.
CPC ..... *G01R 33/4836* (2013.01); *G01R 33/4833* (2013.01); *A61B 5/055* (2013.01);
(Continued)

(58) Field of Classification Search
CPC .. A61B 5/055; G01R 33/5676; G01R 33/543; G01R 33/4833; G01R 33/4836;
(Continued)

(56) References Cited

U.S. PATENT DOCUMENTS

| 4,835,690 A * | 5/1989 | Gangarosa ............. G01R 33/54 |
| | | 324/318 |
| 8,217,648 B2 | 7/2012 | Kachi et al. |

(Continued)

FOREIGN PATENT DOCUMENTS

| EP | 0412819 A2 | 2/1991 |
| JP | 4-309331 | 10/1992 |

(Continued)

OTHER PUBLICATIONS

English translation of JP 2001-340317.*
(Continued)

*Primary Examiner* — Melissa Koval
*Assistant Examiner* — Rishi Patel
(74) *Attorney, Agent, or Firm* — Cooper & Dunham LLP

(57) ABSTRACT

In imaging using 2-dimensional selective excitation pulses, regardless of applications thereof, a technique for obtaining a high quality image is provided.

In the technique, a 2-dimensional selective excitation sequence is carried out while changing a coefficient for determining the cylinder diameter of a region excited by the 2-dimensional selective excitation sequence and a time difference for determining an offset position.

The obtained excitation region and a desired region are compared with each other, and the coefficient and time difference with which the obtained excitation region and the desired region match each other are determined to be the optimum ones.

The determination processing may be performed as an initial adjustment, may be performed according to need in each imaging, or may be performed on a per-application basis.

13 Claims, 23 Drawing Sheets

(51) Int. Cl.
  *A61B 5/055* (2006.01)
  *G01R 33/54* (2006.01)
  *G01R 33/567* (2006.01)

(52) U.S. Cl.
  CPC ........ *G01R 33/4838* (2013.01); *G01R 33/543* (2013.01); *G01R 33/546* (2013.01); *G01R 33/5676* (2013.01)

(58) Field of Classification Search
  CPC . G01R 33/546; G01R 33/4838; G01R 33/483
  USPC ......... 324/307, 309, 318–322; 600/407–422; 382/131, 132
  See application file for complete search history.

(56) References Cited

U.S. PATENT DOCUMENTS

| | | | |
|---|---|---|---|
| 2008/0061780 A1* | 3/2008 | Yamada et al. | 324/309 |
| 2008/0132776 A1* | 6/2008 | Boettcher | 600/410 |
| 2008/0238425 A1 | 10/2008 | Xu et al. | |
| 2009/0175524 A1 | 7/2009 | Kachi et al. | |
| 2011/0196225 A1* | 8/2011 | Hirata et al. | 600/410 |

FOREIGN PATENT DOCUMENTS

| | | |
|---|---|---|
| JP | 6-54820 | 3/1994 |
| JP | 2001-187038 | 7/2001 |
| JP | 2001-340317 | 12/2001 |
| JP | 2005-253885 | 9/2005 |
| JP | 2008-54738 | 3/2008 |
| JP | 2009-72521 | 4/2009 |
| JP | 2009-160273 | 7/2009 |

OTHER PUBLICATIONS

International Search Report in PCT/JP2010/066346.
Japanese official action dated Sep. 9, 2014 in corresponding European patent application No. 2011-534206.
European Search Report dated May 27, 2013 in corresponding European patent application No. 10 82 0408.2.
Nigel P. Davies et al., "Selective arterial spin labeling (SASL): Perfusion territory mapping of Selected feeding arteries tagged using two-dimensional radiofrequency pulses", Mag. Reson. In Med., vol. 29, No. 6, 2003, 1133-1142.
Nigel P. Davies et al., "Calibration of gradient propagation delays for accurate two-dimensional Radiofrequency pulses", Mag. Reson. In Med., vol. 53, No. 1, 2004, 231.
Takahashi et al., "Compensation of multi-dimensional selective excitation pulses using Measured k-space trajectories", Mag. Reson. In Med., vol. 34, 1995, 446.
Boernert P et al., "On spatially selective RF excitation and its analogy with spiral MR image Acquisition", Magma, vol. 7, No. 3, 1998, 166.
A. Rajagopalan, "Two Dimensional Spatially Selective RF Pulse Design Using Spiral Trajectory", EE591 Project Report, 2005, http://ee-classes.usc.edu/ee591/projects/fall05/rajagop.pdf.

* cited by examiner

FIG. 17

| INFORMATION ON APPLICATION | COEFFICIENT A | TIME DIFFERENCE TimeD |
|---|---|---|
| 511 | 512 | 513 |

| CYLINDER SIZE STORING UNIT 536 | | ADJUSTMENT VALUE STORING UNIT 536 | |
|---|---|---|---|
| CYLINDER DIAMETER | OFFSET POSITION | COEFFICIENT A | TIME DIFFERENCE TimeD |
| | | | |
| | | | |

530

MAGNETIC RESONANCE IMAGING APPARATUS AND METHOD FOR ADJUSTING EXCITATION REGION

FIELD OF THE INVENTION

The present invention relates to a technique for magnetic resonance imaging (MRI) capable of measuring a nuclear magnetic resonance (hereinafter referred to as "NMR") signal from hydrogen or phosphorus, etc. in an object to be examined and imaging density distribution or relaxation time, etc. of a nucleus. In particular, the present invention relates to the imaging technique using 2-dimensional selective excitation which selectively excites the region constrained in a given 2-dimensional direction.

DESCRIPTION OF RELATED ART

In MRI, imaging is executed by exciting a predetermined region (local region) by applying a high-frequency magnetic field (RF) pulse with a gradient magnetic field, and reconstructing an image from the echo signal acquired therefrom. In such MRI, a 2-dimensional selective excitation type RF (hereinafter referred to as 2DRF) pulse which is applied with a gradient magnetic field and excites a local region in a cylinder shape is used for various imaging. There are different representative 2DRF pulses such as a navigator echo acquisition pulse for the purpose of monitoring breathing movement (for example, refer to Non-patent Document 1), a pre-saturation pulse for the purpose of signal suppression of a local region (for example, refer to Non-patent Document 2), an inverting pulse for inverting only blood flow of a specified blood vessel (for example, refer to Non-patent Document 3), and a labeling pulse for labeling only blood flow of a specified blood vessel (for example, Non-patent Document 4).

A cylinder-shaped local region to be excited by 2DRF (cylinder excitation region) differs depending on the applications thereof.

The profile of a cylinder excitation region is determined by the cylinder diameter which is the excitation diameter.

Generally, change of the cylinder diameter influences the exciting position (offset position) (for example, refer to Non-Patent Document 5).

PRIOR ART DOCUMENTS

Non-patent Document 1: A. C. Brau et al. Proc. Intl. Soc. Mag. Reson. Med. 17 (2009), p. 4620
Non-Patent Document 2: R. Rakow-Penner et al. Proc. Intl. Soc. Mag. Reson. Med. 16 (2008), p. 3765
Non-Patent Document 3: M. W. Lagemaat et al. Proc. Intl. Soc. Mag. Reson. Med. 17 (2009), P 600
Non-Patent Document 4: S. Konstandin et al. Proc. Intl. Soc. Mag. Reson. Med. 17 (2009), P. 3654
Non-Patent Document 5: J. Pauly et al. "A k-Space Analysis of Small-Tip-Angle Excitation" Journal of Magnetic Resonance 81, 43-56 (1989)

The cylinder excitation region (form and position) is determined by the pulse profile of the 2DRF and the profile of a gradient magnetic field pulse to be applied with the 2DRF. However, even when these profiles are accurately set in the imaging sequence, some minor errors tend to be generated in the region due to characteristic of each device. For example, for monitoring breathing movement, it is sufficient to acquire echo signals from a large region (diaphragm or peritoneum, etc.). Therefore, when 2DRF is used for navigator echo acquisition pulse, the above-described error is not a problem since high accuracy is not required for the size of the cylinder excitation region.

However, in the case that 2DRF is used for inverting or labeling of blood flow in a specified blood vessel, the excitation must be executed accurately using the cylinder diameter corresponding to the diameter of a target blood vessel. For this reason, high accuracy is required in the cylinder excitation region, and minor errors generated in each device drastically affect the image quality.

Considering the above-described circumstance, the objective of the present invention, in imaging using 2-dimensional selective excitation pulses, is to provide a technique for obtaining a high quality image regardless of applications thereof.

BRIEF SUMMARY OF THE INVENTION

The present invention executes a 2-dimensional selective pulse sequence while changing the coefficient for determining the cylinder diameter of the region to be excited by the 2-dimensional selective excitation sequence and the time difference for determining the offset position. By comparing the acquired excitation region and a desired region, the coefficient and the time difference at the time they match is determined to be the optimum ones.

In concrete terms, the present invention provides the magnetic resonance imaging apparatus which collects the echo signals produced by application of a high-frequency magnetic field and a gradient magnetic field in accordance with a predetermined pulse sequence to an object placed in a static magnetic field and reconstructs an image from the collected echo signals, comprising an adjusting unit configured to adjust at least one of the profile or the position of an excitation region by a local excitation sequence.

Also, in the magnetic resonance imaging apparatus, the present invention provides an excitation region adjusting method for adjusting the excitation region upon executing a local excitation sequence, including:

an excitation region adjusting method comprising a profile parameter calculating step of calculating a profile parameter of the local excitation sequence for exciting the profile of the relevant excitation region on the basis of the excitation region set by an operator; and a profile parameter setting step of setting the profile parameter calculated in the profile parameter calculating step to the local excitation sequence, or an excitation region adjusting method, in addition to the previously described excitation region adjusting method, further comprising a position parameter calculating step of calculating the position parameter of the local excitation sequence for exciting the position of the relevant excitation region on the basis of the excitation region set by an operator; and a position parameter setting step of setting the position parameter calculated in the position parameter calculating step to the local excitation sequence.

EFFECT OF THE INVENTION

In accordance with the present invention, it is possible to obtain a high quality image in an imaging using 2-dimensional selective excitation pulses, regardless of applications thereof.

BRIEF DESCRIPTION OF THE DRAWINGS

FIG. 17 is a view for explaining an adjustment table in the second embodiment.

FIG. 21 is a view for explaining a second adjustment value table in the third embodiment.

DETAILED DESCRIPTION OF THE INVENTION

First Embodiment

Figure 1:
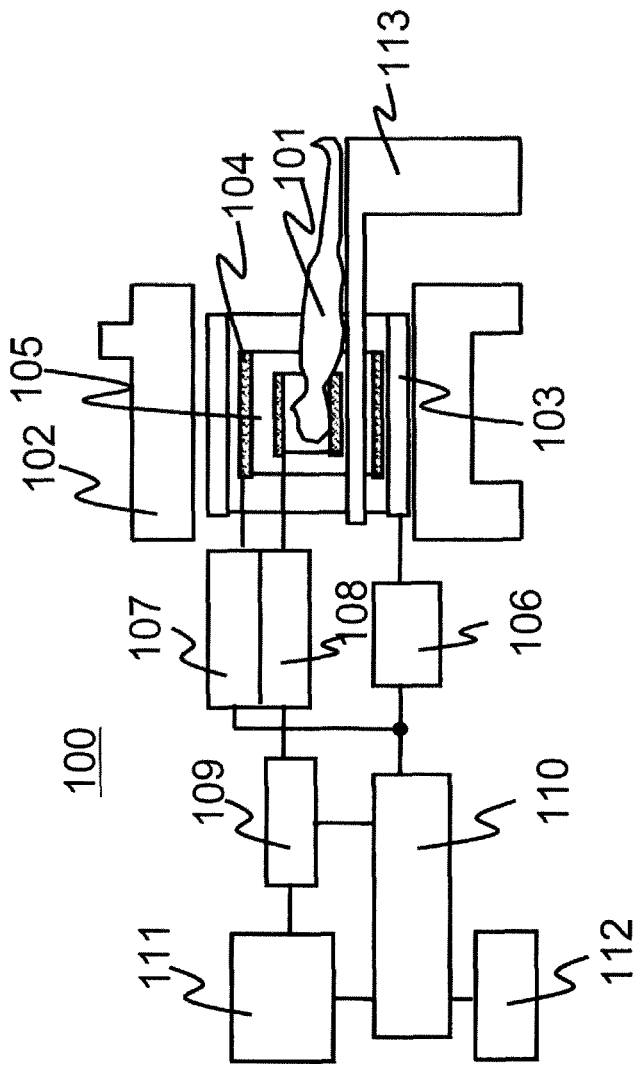
FIG. 1 is a functional block diagram showing the MRI apparatus of a first embodiment.

The first embodiment to which the present invention is applied will be described below. In the entire diagrams for explaining the present invention, the same function parts are represented by the same reference numerals, and the duplicative description thereof is omitted.

First, the configuration of the MRI apparatus in the present embodiment will be described. FIG. 1 is a functional block diagram showing an MRI apparatus 100 in the present embodiment. The MRI apparatus 100 in the present embodiment comprises a magnet 102, a gradient magnetic field coil 103, a high-frequency magnetic field (RF) coil 104, an RF probe 105, a gradient magnetic field power source 106, an RF transmission unit 107, a signal detection unit 108, a signal processing unit 109, a control unit 110, a display unit 111, an operation unit 112 and a bed 113.

The magnet 102 generates a static magnetic field in the surrounding region (examination space) of an object 101. The gradient magnetic field coil 103 is formed by the coils in three directions of X, Y and Z, and the respective coils generate a gradient magnetic field in the examination space in accordance with the signal from the gradient magnetic field power source 106. The RF coil 104 applies (irradiates) an RF in the examination space in accordance with the signal from the RF transmission unit 107. The RF probe 105 detects the MR signal produced by the object 101. The signal received by the RF probe 105 is detected by the signal detection unit 108, processed by the signal processing unit 109 and inputted to the control unit 110. The control unit 110 reconstructs an image by the inputted signals, and displays it on the display unit 111.

Also, the control unit 110 controls operation of the gradient magnetic field power source 106, the RF transmission unit 107 and the signal detection unit 108 via the time chart for control which is stored in advance and the operation unit 112 in accordance with the imaging parameters inputted by the operator. The time chart for control is generally referred to as a pulse sequence. The bed 113 is for the object to be laid down.

The MRI apparatus 100 may also comprise a shim coil for correcting the nonuniformity of static magnetic field in an examination space and a shim power source for supplying electric current to the shim coil.

Currently in MRI, the imaging target is proton which is the main constituent of the object 101. The 2-dimensional or 3-dimensional imaging of the profile or function of a head region, abdominal region or extremities of a body is performed by imaging the spatial distribution of proton density or the spatial distribution of the relaxation phenomenon of the excited proton.

Next, the imaging method by the MRI apparatus 100 in the present embodiment will be described. The RF transmission unit 107 is driven according to the pulse sequence, and a high-frequency magnetic field pulse (RF pulse) is irradiated to the object 101 from the RF coil 104. In this manner, different phase encodes are given to the echo signal produced from the object 101 by the gradient magnetic field, and is detected. The number of phase encodes per one piece of image is usually selected from among 128, 256, 512, etc. The respective echo signals are acquired usually as time-series signals formed by 128, 256, 512 and 1024 sets of sampling data. A piece of MRI image is created by performing 2-dimensional Fourier transform on these acquired data. A gradient magnetic field is applied by the respective gradient magnetic field coils 103, by operating the gradient magnetic field power source 106 according to the pulse sequence.

As for imaging or a pre-pulse sequence in the present embodiment, a 2-dimensional selective excitation (2DRF) pulse is applied with an oscillating gradient magnetic field, using a local excitation pulse sequence (hereinafter referred to as a 2-dimensional selective excitation sequence) for exciting a region which is constrained in the 2-dimensional direction in the form a cylinder shape.

First, the pulse sequence for an excitation part in a 2-dimensional selective excitation sequence of the present embodiment will be described. FIG. 2(a) is an example of the pulse sequence which is the excitation part of a 2-dimensional selective excitation sequence in the present embodiment. Here, the case of a cylinder-shaped excitation in the z-axis direction is shown.

As shown in the diagram, in a 2-dimensional selective excitation pulse sequence 600, by applying a 2DRF pulse 611 with an oscillating gradient magnetic field (Gx) 612 in the x-axis direction and an oscillating gradient magnetic field (Gy) 613 in the y-axis direction, a cylinder-shaped region (cylinder excitation region) in the above-mentioned z-axis direction is excited. The echo signals acquired from the excitation region to which a phase encode is given as described above are sampled in time series and placed in a k-space.

In the present embodiment, in the MRI apparatus 100, the region which is excited by the 2-dimensional selective excitation sequence 600 (cylinder excitation region) is adjusted to be the region intended by an operator. The cylinder excitation region is determined by the diameter of the cylinder excitation region (cylinder diameter) and the position of the cylinder excitation region (offset position). Therefore, the 2-dimensional selective excitation sequence 600 is adjusted so that the cylinder diameter of the cylinder excitation region by the 2-dimensional selective excitation sequence 600 matches the cylinder diameter which is intended by the operator and the offset position thereof matches the offset position intended by the operator.

The adjustment of cylinder diameter is performed by adjusting the profile parameter of the 2-dimensional selective excitation sequence 600 so that the cylinder diameter of a cylinder excitation region which is actually excited by the 2-dimensional selective excitation sequence (actual cylinder diameter) matches the cylinder diameter which is specified by the operator (specified cylinder diameter).

Also, adjustment of the offset position is performed, after the cylinder diameters are matched, by adjusting the positional parameter of the 2-dimensional selective excitation sequence 600 so that the actually excited position (actual offset position) matches the offset position which is specified by the operator (specified offset position).

Figure 3:
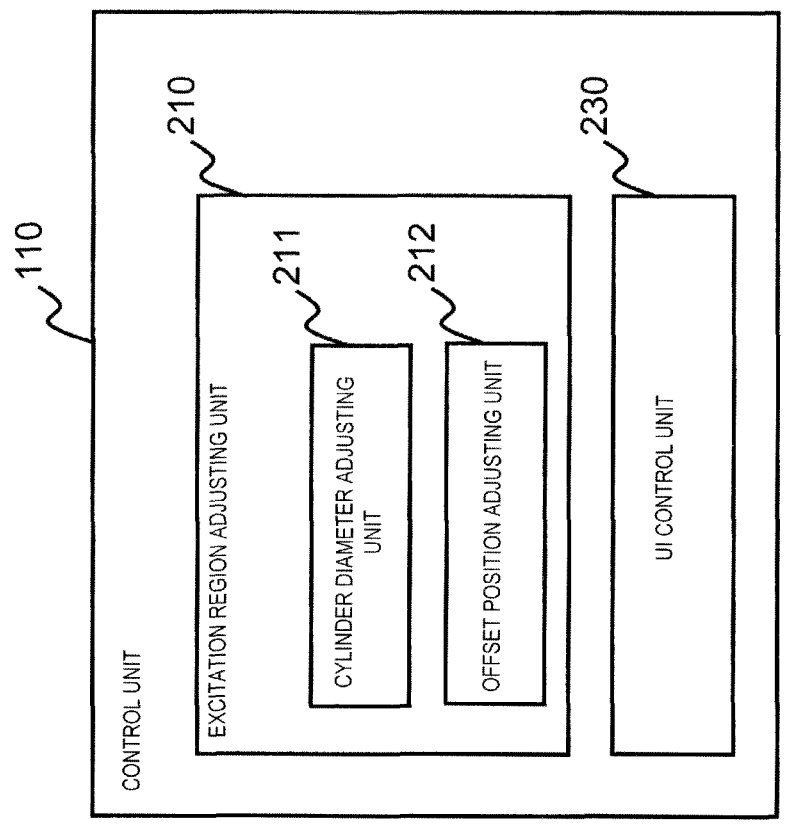
FIG. 3 is a functional block diagram showing apart related to the excitation region adjusting process by a control unit in the present embodiment.

In order to achieve the above-described process, the control unit 110 of the present embodiment comprises an excitement region adjusting unit configured to adjust a cylinder excitation region by the 2-dimensional selective excitation sequence 600. FIG. 3 is a functional block diagram showing the part related to the adjustment of an excitation region by the 2-dimensional selective excitation sequence 600 of the control unit 110 in the present embodiment. As shown in the present diagram, the control unit 110 comprises an excitation adjusting unit 210 and a UI control unit 230. Also, the excitation region adjusting unit 210 comprises a cylinder diameter adjusting unit 211 configured to determine the profile parameter of the 2-dimensional selective excitation sequence 600 for making the cylinder diameter of an excited region to match a desired diameter, and an offset position adjusting unit 212 configured to determine the positional parameter of a 2-dimensional selective excitation sequence for making the offset position to match a desired position.

The control unit 110 is formed by an information processing device comprising a CPU, a memory and a storage device, and these respective components function by the CPU loading the program which is stored in the storage device in advance to the memory and executing the program.

Figure 4:
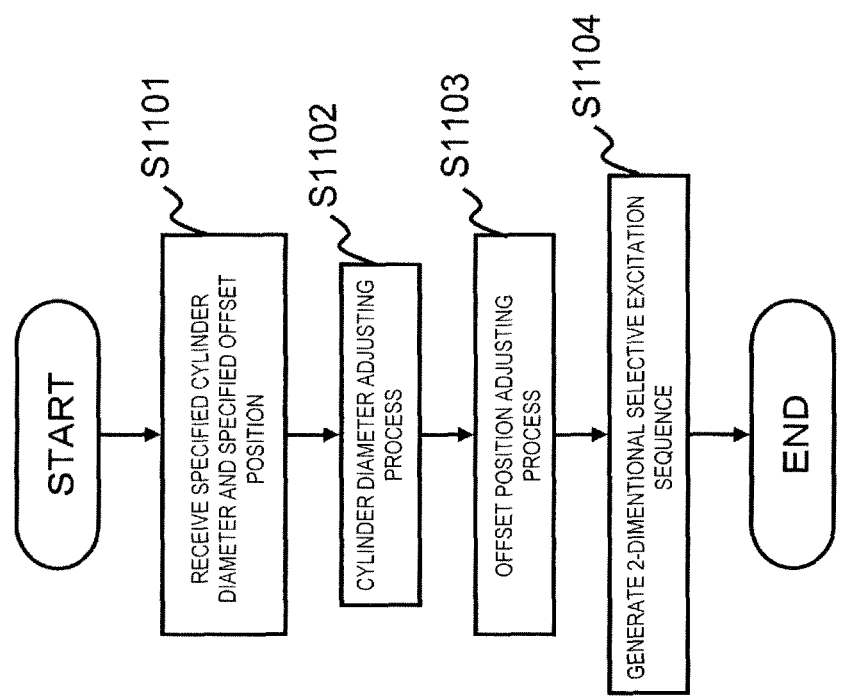
FIG. 4 is a flowchart of the excitation region adjusting process in the present embodiment.

The flow of the excitation region adjusting process by the excitation region adjusting unit 201 in the present embodiment will be described. FIG. 4 is the processing flow of the excitation region adjusting process in the present embodiment. The excitation region adjusting process of the present embodiment starts by receiving the command from an operator to start the process.

Upon receiving the command from the operator to start the process, the excitation region adjusting unit 210 causes the UI control unit 230 to display the screen for indicating a specified cylinder diameter and a specified offset position on the display 111, and receives this input (step S1101). Upon receiving the specified cylinder diameter and the specified offset position via the specification screen, the UI control unit 230 notifies the received information to the cylinder diameter adjusting unit 211 and the offset position adjusting unit 212.

The cylinder diameter adjusting unit 211 executes the cylinder diameter adjusting process for adjusting the cylinder diameter (step S1102). After executing the cylinder diameter adjusting process, the offset position adjusting unit 212 executes the offset position adjusting process for adjusting the offset position (step S1103). The excitation region adjusting unit 210 generates the 2-dimensional selective excitation sequence by setting the acquired result (step S1104), and completes the process.

Figure 5:
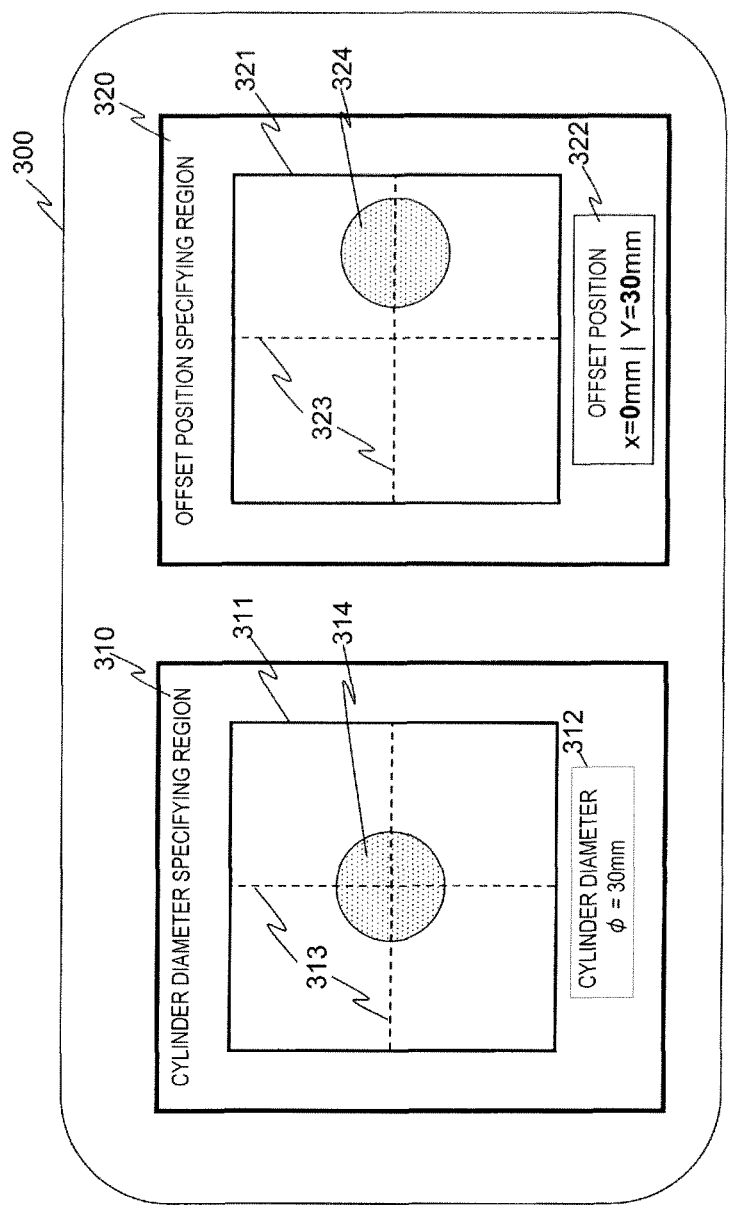
FIG. 5 is a view for explaining a specification screen in the present embodiment.

First, the specification screen wherein the UI control unit 230 displays information on the display unit 111 will be described in the excitation region adjusting process. FIG. 5 is a view for explaining the specification screen 300 in the present embodiment. As shown in the diagram, the specification screen 300 in the present embodiment comprises a cylinder diameter specifying region 310 for specifying the cylinder diameter and an offset position specifying region 320 for specifying the offset position.

The cylinder diameter specifying region 310 comprises a diameter specifying region 311 and a numeric value display region 312. The diameter specifying region 311 comprises a guideline 313 for indicating the center of an irradiation region by 2DRF.

On the diameter specifying region 311, a cylinder cross-section display 314 for showing a cross section of the cylinder is displayed in advance. Here, a circle is displayed. The operator adjusts the size of the cylinder cross-section display 314 which is displayed on the diameter specifying region 311 using a device such as a mouse provided in the operation unit 112. The cylinder diameter acquired as the result of adjustment is displayed by a numeric value on the numeric value display region 312.

The cylinder diameter may also be inputted by the numeric value via the numeric value display region 312. In this case, the size of the cylinder cross-section display 314 is changed and displayed on the diameter specifying region 311, so as to match the cylinder diameter which is inputted by the operator via the numeric value display region 312.

The offset position specifying region 320 comprises a position specifying region 321 and a numeric display region 322. The position specifying region 321 comprises a guideline 323 which indicates the center of an irradiation region. On the position specifying region 321, the cylinder cross-section display 324 for showing a cross section of a cylinder is displayed. The size of the cylinder cross-section display 324 is changed according to the size of the cylinder diameter which is specified in the cylinder diameter specifying region 310. The operator adjusts the position of the cylinder cross-section display 324 which is displayed on the position specification screen 321 using a device such as a mouse provided to the operation unit 112. The adjusted position is displayed by numeric value on the numeric value display region 322. Here, the position specifying region 321 is represented by the x-axis and the y-axis, and the values of the x-coordinates and the y-coordinates in the case that the center of an irradiation region is set as the center of these coordinate axes is displayed.

In the offset position specifying region 320, the offset position may also be inputted by the numeric value via the numeric value display region 322. In this case, the position of the cylinder cross-section display 324 is changed and displayed on the position specifying region 321, so as to match the offset position which is inputted by the operator via the numeric value display region 322.

While the case that the cylinder diameter specifying region 310 and the offset position specifying region 320 are simultaneously displayed on the specification screen 300 is exemplified here, the configuration of the specification screen 300 is not limited thereto. It may be configured so that only one of the cylinder diameter specifying region 310 and the offset position specifying region 320 may be displayed. In this case, the UI control unit 230 displays one of them according to the command from the operator.

Next, the cylinder diameter adjusting process by the above-described cylinder diameter adjusting unit 211 will be described in detail.

In the 2-dimensional selective excitation sequence 600, when the application time of the 2DRF pulse 611 is set as T, a scan position $(k_x(t), k_y(t))$ in a k-space at time $t(0 \leq t \leq T)$ can be expressed by the following equation (1).

[Equation 1]

$$k_x(t) = A\left(1 - \frac{t}{T}\right)\cos\frac{2\pi nt}{T}$$
$$k_y(t) = A\left(1 - \frac{t}{T}\right)\sin\frac{2\pi nt}{T}$$

(1)

Here, n is a positive integer which is 1 or more, and represents the number of rotations in the k-space. A is a coefficient, which defines the size of the k-space. By the equation (1), scan position $(k_x(t), k_y(t))$ in a k-space changes along with the change of coefficient A, and the size of k-space to be selected (frequency band) also changes. In other words, when a coefficient A increases, the k-space for scanning takes up a wider frequency band, and when a coefficient A is small, the k-space takes up a narrower frequency band. Along with the change, the size of actual space to be excited, i.e. the cylinder diameter of the cylinder excitation region also changes.

In the cylinder diameter adjusting process of the present embodiment, an actual cylinder diameter RAr determines the coefficient A to be a specifying cylinder diameter SPr.

In the equation (1), when the coefficient A is changed, k(t) is also changed. Here, the relationship between gradient magnetic field G(t) and k(t) can be expressed as the equation (2).

[Equation 2]

$$\vec{G}(t) = \frac{1}{\gamma}\vec{k}(t)$$
$$\vec{k}(t) = -\gamma\int_t^T \vec{G}(s)\,ds$$

(2)

Here, γ is the gyromagnetic ratio (constant number). In this manner, gradient magnetic field G(t) is proportional to the time differentiation of k(t). Therefore, since the coefficient A is the coefficient related to the amplitude of gradient magnetic field (t), particularly the amplitude of gradient magnetic field G (t) is determined by setting the value of the coefficient A. In the 2-dimensional selective excitation sequence 600 of the present embodiment, the value of coefficient A is set and the waveform of gradient magnetic field Gx212 and gradient magnetic field Gy213 is determined in the 2-dimensional selective excitation sequence 600.

Figure 6:
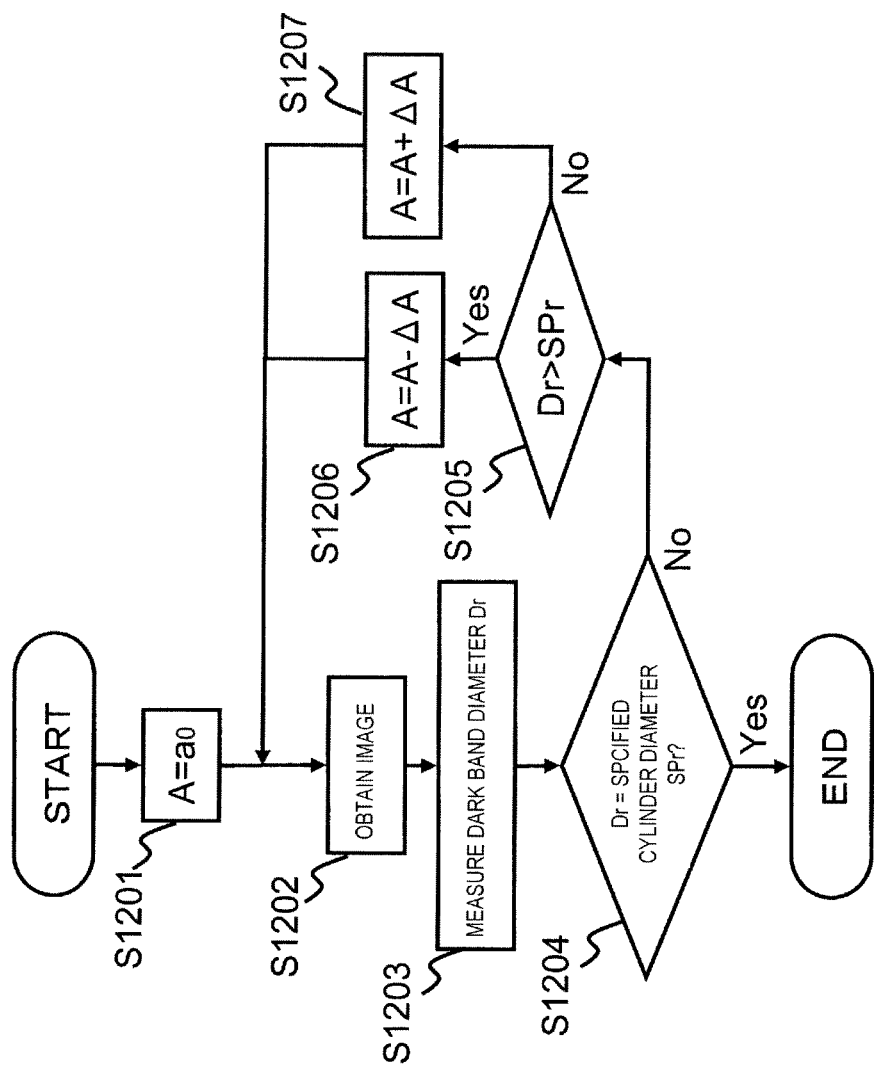
FIG. 6 is a flowchart of the cylinder diameter adjusting process in the present embodiment.

The cylinder diameter adjusting process by the cylinder diameter adjusting unit 211, i.e. the method for determining coefficient A will be described below. FIG. 6 is a processing flow of the cylinder diameter adjusting process in the present embodiment. First, an initial value $a_0$ is set as the coefficient A (step S1201). The initial value $a_0$ is previously set and stored in a device such as a storage device. The coefficient A is set as $a_0$, and an image is obtained using the 2-dimensional selective excitation sequence 600 with the acquired gradient magnetic fields Gx212 and Gy213 (S1202). Image acquisition using the 2-dimensional selective excitation sequence 600 is executed, for example by setting the excitation part of the 2-dimensional selective excitation sequence 600 as a pre-saturation pulse, prior to the general sequence for obtaining images (referred to as an image acquisition sequence). At this time, 2DRF is applied with great intensity, for example by setting the flip angle at about 90 degrees. In this manner, the cylinder excitation region which is excited in a cylinder shape by the 2-dimensional selective excitation sequence 600 remains on the obtained image as a signal weakened region (dark band). The diameter of this dark band is the actual cylinder diameter RAr.

Next, a diameter Dr of the dark band on the obtained image is measured (step S1203). Then a diameter Dr of the dark band and a specified cylinder diameter SPr are compared (step S1204 and step S1205). If the diameter Dr of the dark band and the specified cylinder diameter SPr match, the process is completed. Here, a predetermined tolerance range may be set in addition to the case of perfect match. For example, if the diameter Dr of the dark band is within the previously set range centered on the specified cylinder diameter SPr, the diameter is determined as matched.

On the one hand, when the diameter Dr of the dark band is larger than the specified cylinder diameter SPr, a predetermined value (for example, Δa) is subtracted from the coefficient A (A=A−Δa) (step S1206), and the process returns to step S1202. On the other hand, when the diameter Dr of the dark band is smaller than the specified cylinder diameter SPr, a predetermined value (for example, Δa which is the same as the above-described predetermined value) is added to the coefficient A (A=A+Δa) (step S1207), and the step returns to step S1202. Δa is also stored in the storage device.

Finally by the above-described procedure, the value of coefficient A is acquired at which the actual cylinder diameter RAr and the specified cylinder diameter SPr are equal.

Here, the method for measuring the cylinder diameter (diameter Dr of the dark band) on the obtained image (hereinafter referred to as a phantom image) in the above-described step S1203 will be described referring to FIG. 7.

Figure 7:
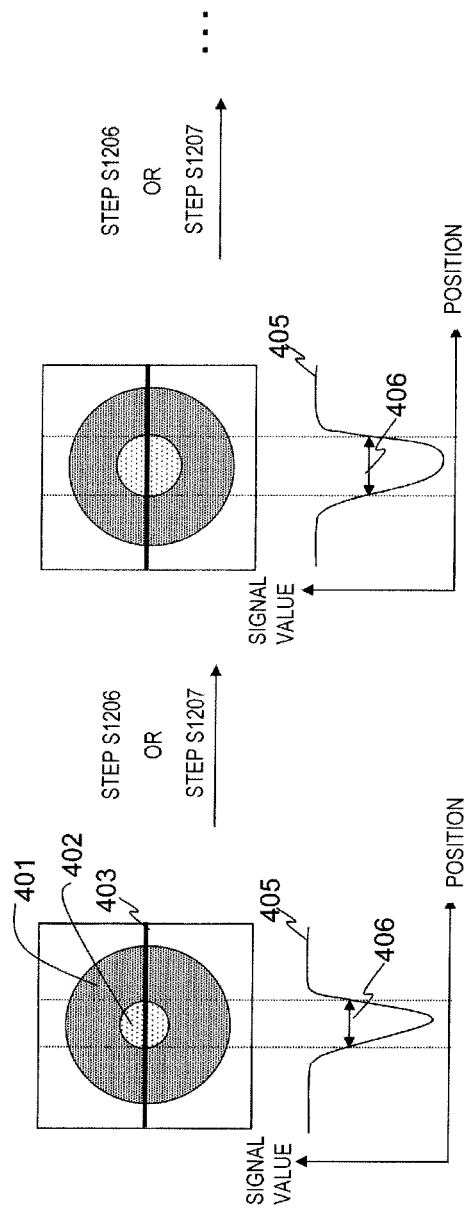
FIG. 7 is a view for explaining the cylinder diameter measuring method in the present embodiment.

The upper part of FIG. 7 is an example of an obtained phantom image 401. When the application position (center position) of the 2-dimensional selective excitation (cylinder excitation) is set as the center of an FOV, a dark band 402 is generated at the center of the phantom image 401. The signal profile of a line 403 which passes through the center of the dark band 402 is measured. An obtained signal profile 405 is displayed at the lower part of FIG. 7. The obtained signal profile 405 is scanned, and a size 406 of the region in which the signal value is decreased is measured, and the measurement result is set as the cylinder diameter (diameter Dr of the dark band). As for the region in which the signal value is decreased, for example a half bandwidth can be used.

As shown in the present diagram, upon repeating the above-described process, when the coefficient A is changed via step S1206 or step S1207, the profile of the signal profile 405 is changed, and the width of the size 406 acquired as the diameter Dr of the dark band is also changed.

Next, the offset position adjusting process by the offset position adjusting unit 212 in step S1103 will be described. In the case that the center of the cylinder excitation region by the 2-dimensional selective excitation sequence 600 is offset from a static magnetic field center $P_0$ to a position P, magnetic state ($M_{xy}$) of a point (x,y) can be expressed by the following equation (3).

[Equation 3]

$$M_{xy}(P) = \gamma M_0 \int_0^T B_1(t) e^{i(P-P_0)\vec{k}(t)} dt \quad (3)$$

Here, $M_0$ is the magnetic state in the static magnetic field center $P_0$, magnetization γ is the gyomagnetic ratio (constant number), and $B_1$(t) is the waveform of the 2DRF pulse 611 to be irradiated by the 2-dimensional selective excitation sequence 600. As shown in the present equation, even when the offset positions are the same, if the state of $B_1$(t) is different at a certain timing, the state of an actual excited magnetization $M_{xy}$ is changed.

Also, waveform $B_1$(t) of the 2DRF pulse 611 can be expressed by the following equation (4) using weighting function W(k) and the modulated gradient magnetic field G(t) to be applied for selecting a region (gradient magnetic field 612Gx and gradient magnetic field 613Gy).

[Equation 4]

$$B_1(t) = W(\vec{k}(t)) |\gamma \vec{G}(t)| \quad (4)$$

In the equation (4), by changing the profile of a gradient magnetic field G(t) at a certain timing t (gradient magnetic field 612Gx and gradient magnetic field 613Gy), waveform. $B_1$ (t) of the 2DRF pulse 611 can be changed, and magnetization $M_{xy}$ is also changed with them. In other words, the offset position changes when the relationship between waveform $B_1$(t) of the 2DRF pulse 611 and the gradient magnetic field G(t) (gradient magnetic field 612Gx and gradient magnetic field 613Gy) changes at a certain timing.

Figure 2:
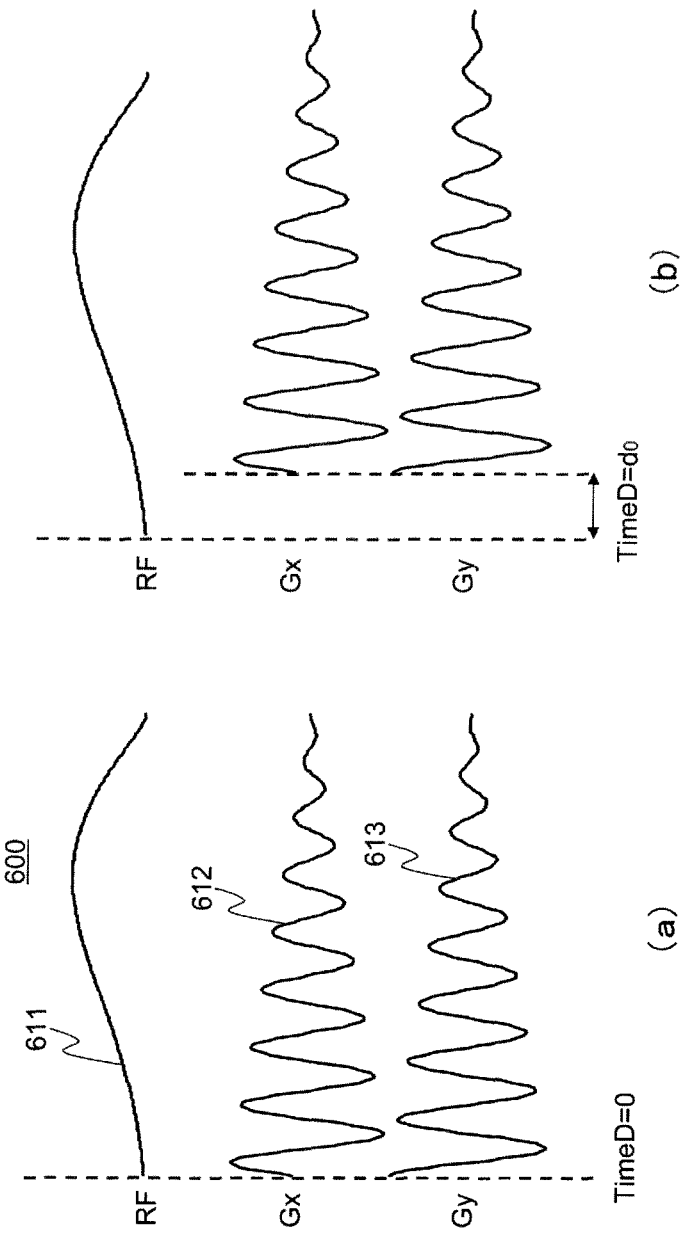
FIGS. 2 (a) and (b) are sequence diagrams showing the 2-dimensional selective excitation sequence of the present embodiment.

Accordingly, the present embodiment changes the relationship between the 2DRF pulse 611 at time t and the intensity of the gradient magnetic fields 612 and 613, and fine adjusts an actual offset position RA of to match the specified offset position SP of. The relationship between the 2DRF pulse 611 and the intensity of the gradient magnetic fields 612 and 613 is changed, as shown in FIG. 2 (b), by shifting the starting times of the 2DRF pulse 611 and the gradient magnetic fields 612 and 613 in the 2-dimensional selective excitation sequence 600. When the shift length of the application starting time of the gradient magnetic fields 612 and 613 from the application starting time of the 2DRF pulse 611 is set as time difference TimeD, the value of time difference TimeD at which the actual offset position RA of matches the specified offset position SP of is determined in the offset position adjusting process.

The phase of the 2DRF pulse 611 can be expressed by the following equation (5) using $k_x$ (t) and $k_y$ (t) determined in the above-described cylinder diameter adjusting process.

[Equation 5]

$$RF\text{phase} = \phi(t) = \Delta x^* k_x(t) + \Delta y^* k_y(t) \quad (5)$$

Figure 8:
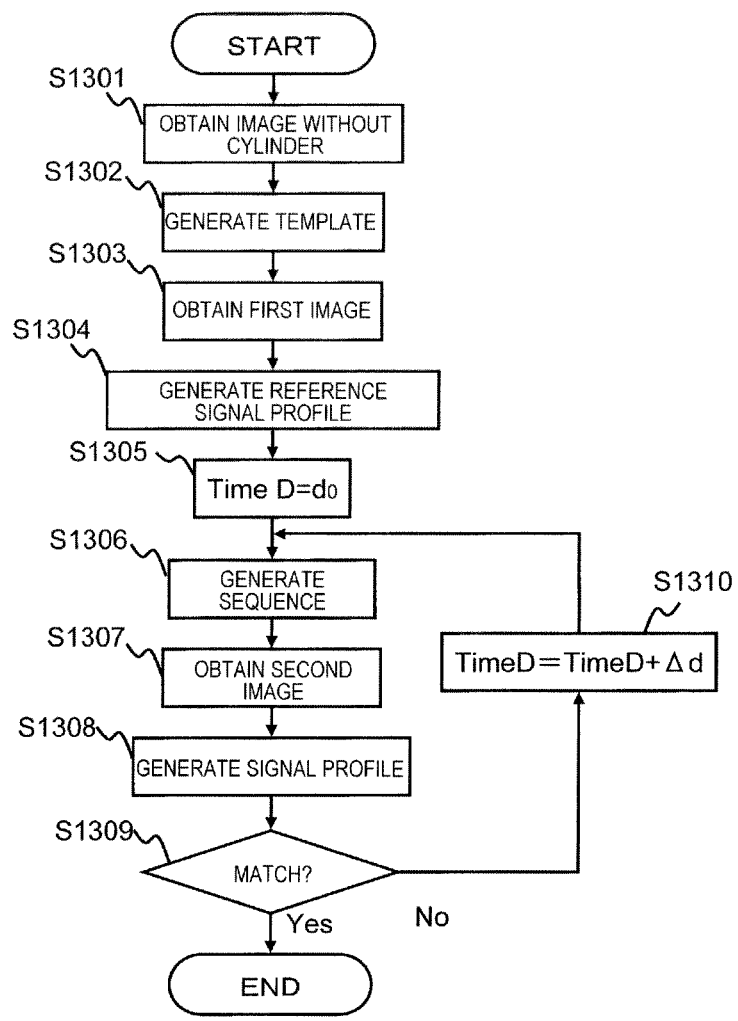
FIG. 8 is a flowchart of the offset position adjusting process in the present embodiment.
Figure 9:
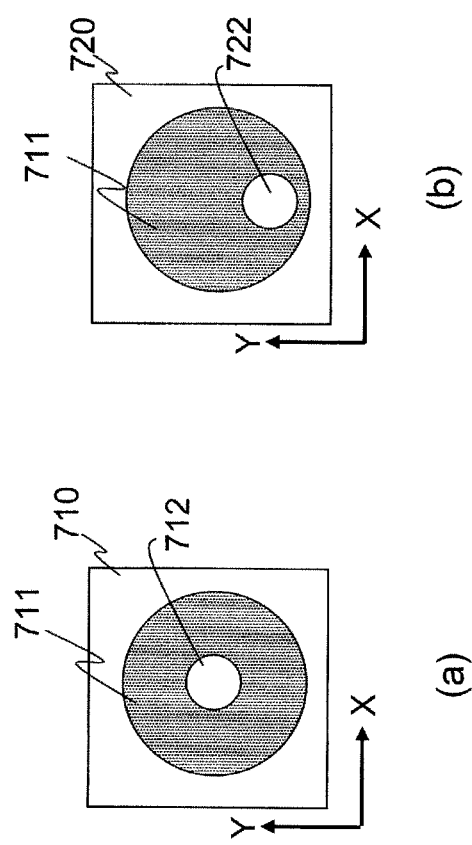
FIGS. 9 (a) and (b) are views for explaining the template in the offset position adjusting process of the present embodiment.
Figure 10:
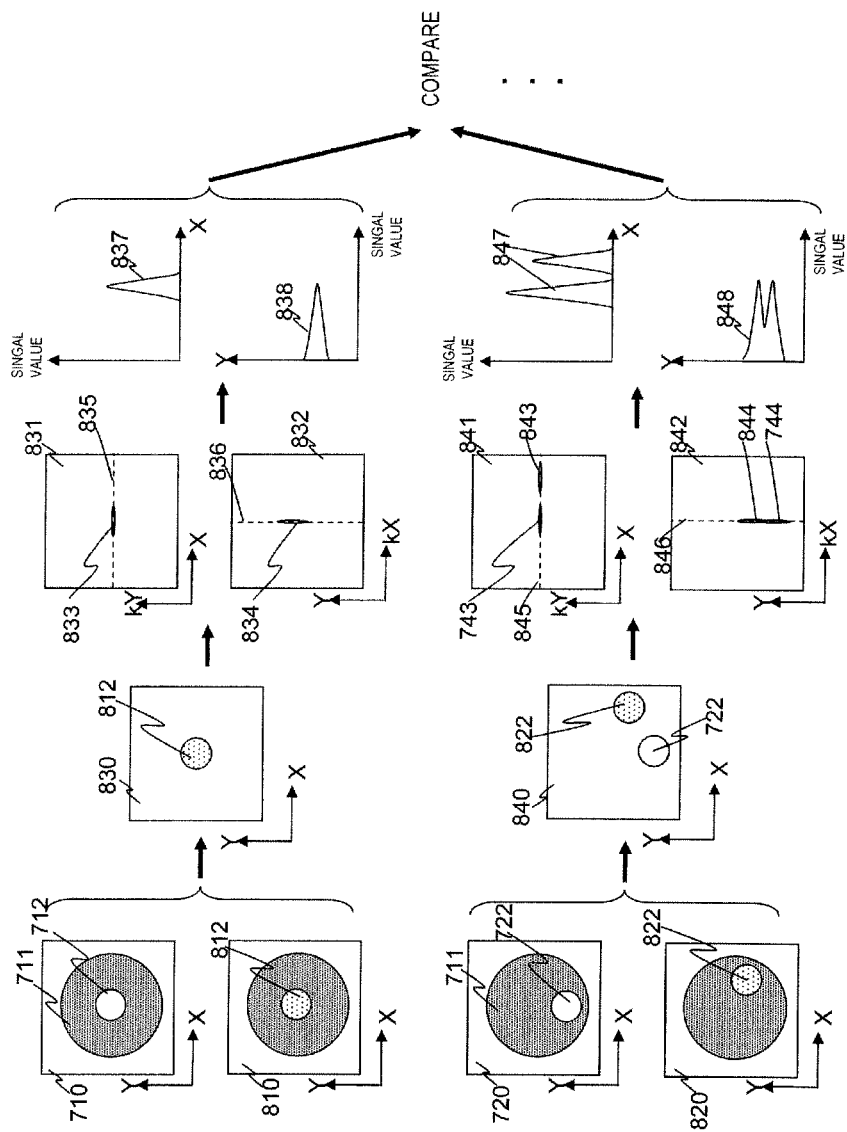
FIG. 10 is a view explaining the offset position adjusting process in the present embodiment.

The offset position adjusting process by the offset position adjusting unit 212, i.e. the method for determining time difference TimeD will be described below. FIG. 8 is a processing flow of the offset position adjusting process. Also, FIG. 9 and FIG. 10 are views for explaining the offset position adjusting process.

First, an image is obtained without using the 2-dimensional selective excitation sequence 600 at the same time (no cylinder image) (step S1301). For example, an image is obtained using the image acquisition sequence which is used in the above-described cylinder diameter adjusting process.

From the obtained image, a template is generated for confirming the consistency of the specified offset position and the actual offset position (step S1302). Here, as shown in FIGS. 9 (a) and (b), two templates of a first template 710 and a second template 720 are generated. The first template 710 is obtained, in an acquired image 711, by filling a region 712 which centers on the center of an FOV that is the center of the static magnetic field and has the diameter of the specified cylinder diameter SPr with 0 data. This is the condition that the 2-dimensional selective excitation sequence without offset is imitated. Also, the second template 720 is obtained, in an acquired image 711, by filling a region 722 which centers on the offset position SP of specified in step S1011 of the excitation region adjusting process and has the diameter of the specified cylinder diameter SPr with 0 data.

Next, a first image 810 using the 2-dimensional selective excitation sequence 600 at the same time capable of specifying a dark band is obtained (step S1303). Here, in the same manner as the cylinder diameter adjusting process, the 2DRF pulse 611 of the 2-dimensional selective excitation sequence 600 is set as the pre-saturation pulse to execute the image acquisition sequence. The first image 810 is obtained in the condition without offset. Then a signal profile to be the reference for confirming the consistency of the offset position (reference signal profile) is generated from the first template 710 and the first image 810 (step S1304).

Here, the procedure for creating the reference signal profile will be described using FIG. 10. First, the difference between the first template 710 and the first image 810 is calculated so as to obtain a first difference image 830. Here, since the cylinder diameter is already adjusted, the region in which the first template 710 is filled with 0 data and the dark band region 812 of the first image 810 coincide with each other. Therefore, the first difference image 830 becomes an image in which the signals exist only in the dark band region 812.

Then the reference signal profile is generated from the first difference image 830 in the x-axis direction and the y-axis direction. In concrete terms, an image 831 which is inverse Fourier transformed from the first difference image 830 in the y-axis direction and an image 832 which is inverse Fourier transformed in the x-axis direction are generated. Here, images 833 and 834 are obtained in which the image of the dark band region 812 is integrated at a pixel in the respectively inverse Fourier transformed directions. Signal profiles 837 and 838 of lines 835 and 836 along the direction that are not inverse Fourier transformed (the x-axis direction if the image is obtained by inverse Fourier transforming in the y-axis direction, and the y-axis direction if the image is obtained by inverse Fourier transforming in the x-axis direction) including the images 833 and 834 are created as the reference signal profiles.

Next, an initial value $d_0$ is set on time difference TimeD between the application starting time of the 2DRF pulse 611 and the application starting time of the oscillating gradient magnetic fields 612 and 613 (step S1305) for the time that the 2-dimensional selective excitation sequence 600 is executed. The initial value $d_0$ is set in advance and stored in a storage device, etc. Then as shown in FIG. 2(*b*), the 2-dimensional selective excitation sequence in which the application times of the gradient magnetic fields 612 and 613 are displaced for the portion of time difference TimeD is generated (step S1306). Then the image acquisition sequence is executed using this 2-dimensional selective excitation sequence at the same time, and the second image 820 is obtained (step S1307). It is assumed that the 2-dimensional selective excitation sequence used here is the same as the 2-dimensional selective excitation sequence 600 used at the time of obtaining the above-mentioned first image 810 with the exception of the starting time of the gradient magnetic fields 612 and 613.

Then a second difference image 840 is generated from the second template 720 and the second image 820, and the signal profiles in the x-axis direction and the y-axis direction are generated (step S1308). Here, the method for generating the signal profiles is the same as the one for generating them from the above-mentioned first difference image.

That is, the difference between the second template and the second image 820 is calculated so as to obtain the second difference image 840. At this time, if the timing to start application of a gradient magnetic field is appropriate, the dark band region of the second image 820 on the obtained difference image 840 coincides with the dark band region 722 which is set on the second template 720. On the other hand, if the gradient magnetic field application start timing is not appropriate, positional displacement is generated on the obtained difference image 840 between the dark band region 822 of the second image 820 and the dark band region 722 on the second template 720, and two dark band regions 722 and 822 are generated on the second difference image 840.

From the second difference image 840, an image 841 which is inverse Fourier transformed in the y-direction and an image 842 which is inverse Fourier transformed in the x-direction are generated. Then an image is obtained wherein the image of the dark band region is integrated at a pixel in the inverse Fourier transformed direction. Here, images 743 and 744 obtained from the dark band region 722 and images 843 and 844 obtained from the dark band region 822 are obtained.

In the image 841, a signal profile 847 of a line 845 along the direction which is not inverse Fourier transformed including the images 743 and 843 is acquired. Also, in the image 842, a signal profile 848 a line 846 along the direction which is not inverse Fourier transformed including the images 744 and 844 is acquired.

Then the acquired signal profiles 847 and 848 are compared with the reference signal profiles 837 and 838 which are respectively in the same directions, and whether the excited positions are matched or not is determined (step S1309).

Figure 11:
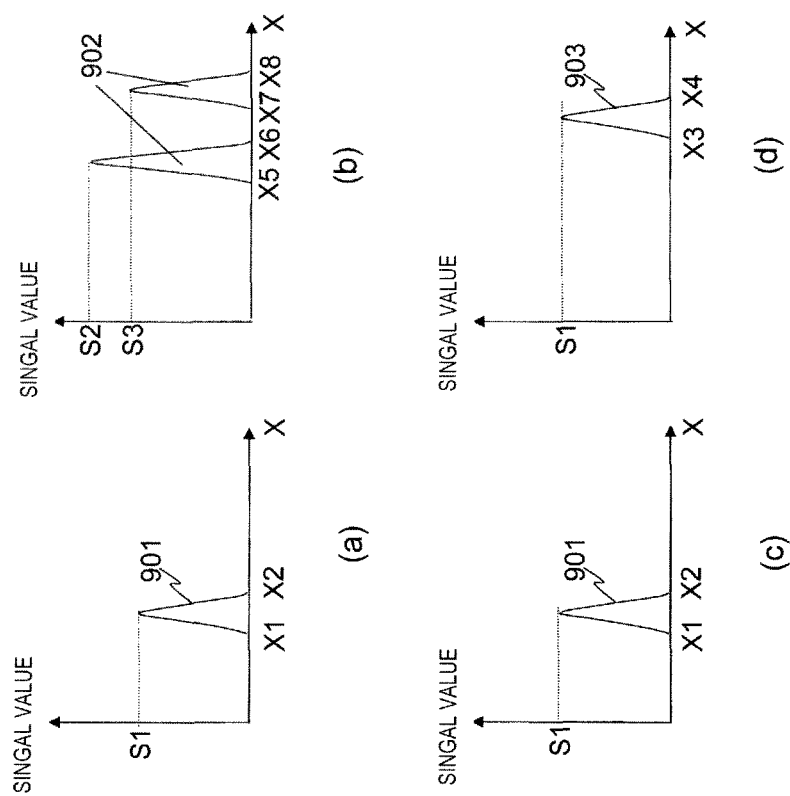
FIGS. 11 (a)~(d) are views for explaining the method in the present embodiment for determining whether or not the profile signals match each other.

The consistency of the excited positions is determined by the consistency of the compared signal profiles. An example of the determination method is shown in FIG. 11. As shown in the present diagram, the comparison of signal profiles is executed by replacing the respective signal values with the histograms in the range where the signal values are distributed. In other words, the distribution range is compared with the signal intensity, and if they match the consistency is determined regardless of the distributional positions. All the rest is determined as inconsistent. Additionally, determination of consistency may be performed by setting an admissible error range so that the value of which the difference is within the admissive error range can be determined as consistent even if the values are not exactly the same.

For example, a reference signal profile 901 formed by one peak in which the distribution range is from X1 to X2 and the signal intensity is S1 shown in FIG. 11(*a*) is determined as inconsistent with a comparative signal profile 902 shown in FIG. 11(*b*). It is because the comparative signal profile 902 shown in FIG. 11 (*b*) is formed by a peak in which the distribution range is from X5 to X6 and the signal intensity is S2 and a peak in which the distribution range is from X7 to X8 and the signal intensity is S2, and the number of peaks is different from the reference signal profile 901. On the other hand, the reference signal profile 901 shown in FIG. 11(*c*) and a comparative signal profile 903 shown in FIG. 11(*d*) are determined as consistent if the distribution ranges |X2-X1| and |X4-X3| are consistent, since they both have the signal intensity of S1.

In step S1309, if determination is made as consistent, the process is completed. On the other hand, if determination is made as inconsistent, a predetermined value (for example, $\Delta d$) is added to TimeD (TimeD=TimeD+$\Delta d$) (step S1310), the step is returned to S1306 and the process is repeated. Here, $d\Delta$ is also stored in a storage device in advance.

As for the admissive range for confirming the consistency, a stored predetermined value may be used or the spatial resolution in accordance with the imaging condition of the image acquisition sequence may be used for the calculation thereof.

The excitation region adjusting unit 210 in the present embodiment determines the pulse sequence of the 2-dimensional selective excitation sequence using the coefficient A and time difference TimeD acquired in the above-described procedure.

As described above, in accordance with the present embodiment, it is possible to automatically and accurately correct an error of the size of a cylinder-shaped excitation region attributed to the characteristic of each device. Thus, the region which is intended by an operator can be accurately excited by using the 2-dimensional selective excitation pulse, whereby the effect of a 2DRF pulse can be maximized without additional burden on an object and images with high quality can be obtained.

While specification of an offset position is executed right after the cylinder diameter is specified in the above-described embodiment, the timing is not limited thereto. Specification of an offset position may also be executed, after the cylinder diameter is specified and the coefficient A is determined, right before adjusting the offset position.

Also, while the case in which the profile of the cross-section which is parallel to the xy-plane of a cylinder excitation region is a circle is exemplified in the above-described embodiment, the profile is not limited thereto. For example, an ellipse having respectively different cylinder diameters in 2-axes directions may also be used. In this case, for example, in the case that the cylinder diameter is measured in the cylinder diameter adjusting process, both the long-axis direction and the short-axis direction of the ellipse are measured, and an actual cylinder diameter RAr is made to approximately match with a specified cylinder diameter SPr in the same manner as the above-described embodiment. The procedure in this case will be described. Here, the coefficient of kx(t) is set as Ax, the coefficient of kx is set as Ax, and the coefficient of ky(t) is set as Ay.

Figure 12:
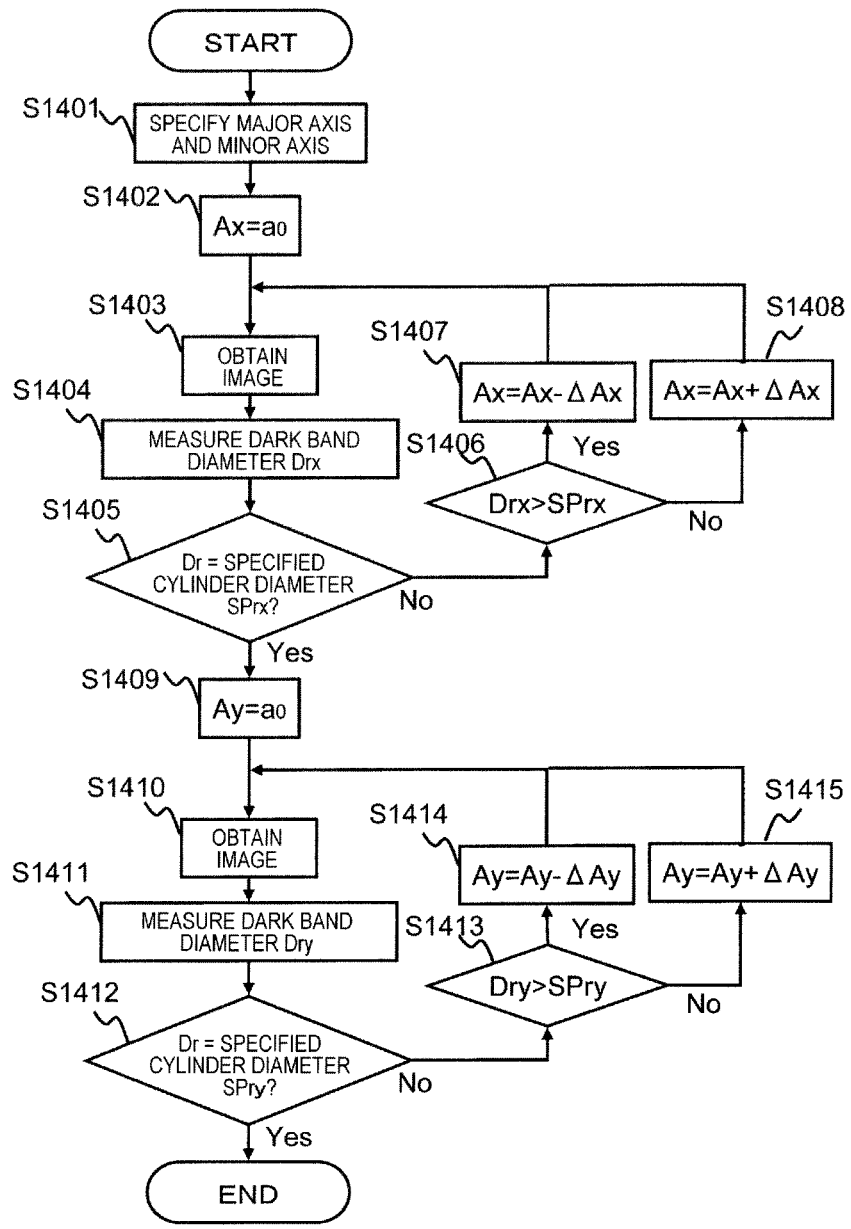
FIG. 12 is a flowchart of another example of the cylinder diameter adjusting process in the present embodiment.

FIG. 12 is a processing flow of the cylinder diameter adjusting process in this case. First, the cylinder diameter adjusting unit 211 specifies the major-axis direction and the minor-axis direction of the cylinder diameter in a 2-dimensional selective region (step S1401). Then, with respective to the axis-direction specified as the minor-axis direction (here, the x-axis direction as an example), the same process from step 1201 to step S1207 in the above-described cylinder diameter adjusting process is executed as from step S1402 to step S1408, and the coefficient Ax in the x-axis direction is determined.

At this time, in step S1404, a diameter Drx in the x-axis direction is measured, and a specified cylinder diameter SPrx in the minor-axis direction (x-axis direction) is used for comparison in steps S1405 and S1406. Further, for the difference to be used for addition and subtraction in steps S1407 and S1408, ΔAx which is stored in advance is used for the x-axis direction.

Figure 13:
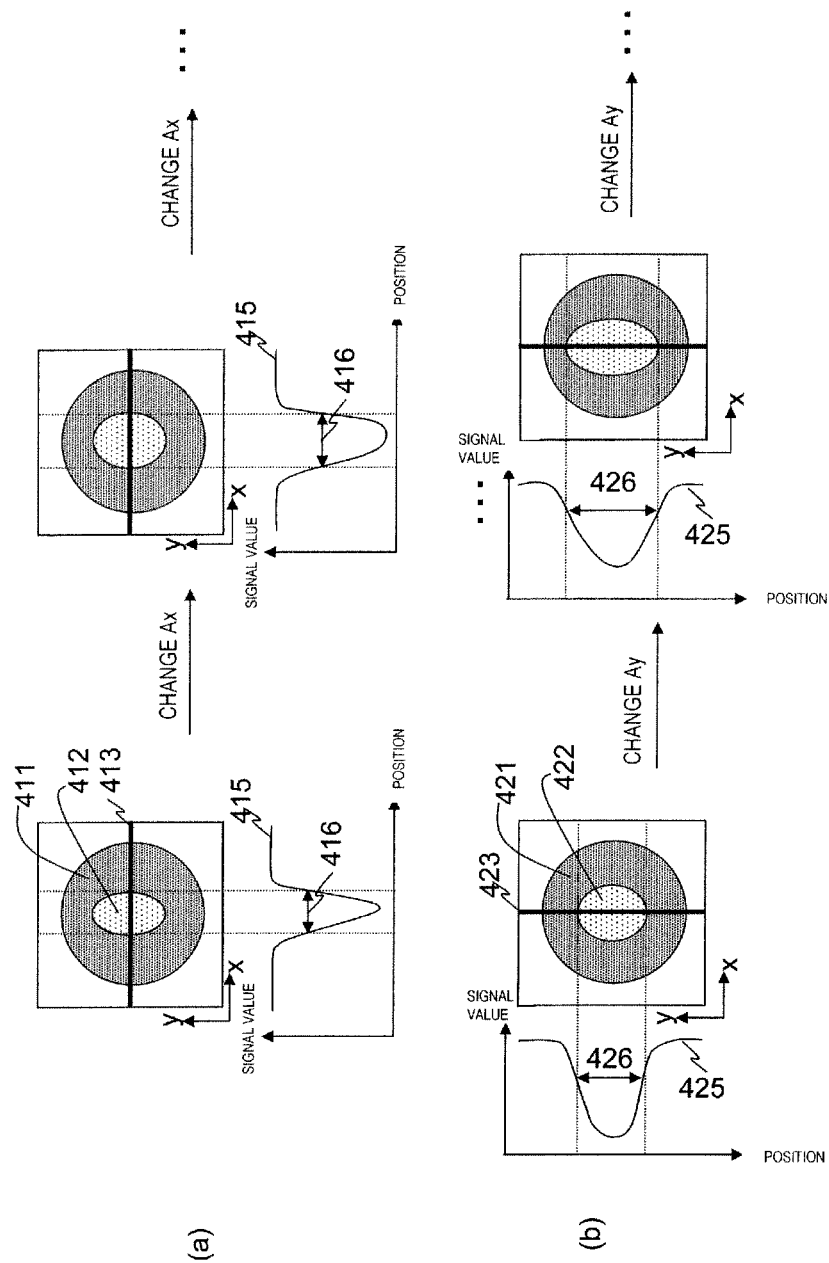
FIGS. 13 (a) and (b) are views for explaining another example of the cylinder diameter measuring method in the present embodiment.

Also, measurement of the cylinder diameter in the x-axis direction on the obtained phantom image 411 in step S1404 will be described referring to FIG. 13(a). The upper part of FIG. 13(a) is the phantom image 411 obtained in step S1403. When the application position (center position) of a 2-dimensional selective excitation (cylinder excitation) is assumed to be the center of an FOV, a dark band 412 is generated in the center of the phantom image 411. The signal profile of a line 413 which passes through the center of the dark band 412 and is parallel to the x-axis direction is measured. The acquired signal profile 415 is shown in the lower part of FIG. 13(a). An acquired signal profile 415 is scanned, a size 416 of the region by which the signal value is decreased is measured, and set as the cylinder diameter (diameter Drx of the dark band). The acquired signal profile 415 is shown in the lower part of FIG. 13(a). The acquired signal profile 415 is scanned, the size 416 of the region of which the signal value is decreased is measured, and is set as the cylinder diameter (diameter Drx of the dark band). As for the region in which the signal value is decreased, for example a half bandwidth can be used.

As shown in the present diagram, upon repeating the above-described process, when the coefficient Ax is changed via step S1407 or step S1408, the profile of the signal profile 415 is changed, and the width of the size 416 which is acquired as the diameter Drx of the dark band is also changed.

Next, with respect to the axis direction set as the major-axis direction (y-axis direction), the same process from step S1201 to step S1206 in the above-described cylinder diameter adjusting process is executed as from step S1409 to step S1415, and a coefficient Ay in the y-axis direction is determined. At this time, in step S1411, a diameter Dry in the y-axis direction is measured, and a specified cylinder diameter Spry in the major-axis direction (y-direction) is used for the comparison in steps S1412 and S1413. Further, for the difference to be used for addition and subtraction in steps S1414 and S1415, ΔAy which is stored in advance is used for the y-axis direction.

Also, measurement of the cylinder diameter in the y-axis direction on the phantom image 421 obtained in step S1411 will be described referring to FIG. 13(b). The upper part of FIG. 13(b) is the phantom image 421 obtained in step S1410. When the application position (center position) of a 2-dimensional selective excitation (cylinder excitation) is assumed to be the center of an FOV, a dark band 422 is generated in the center of the phantom image 421. The signal profile of a line 423 passing through the center of the dark band 422 which is parallel to the y-axis direction is measured. The acquired signal profile 425 is shown in the lower part of FIG. 13(b). The acquired signal profile 425 is scanned, a size 426 of the region by which the signal value is decreased is measured, and set as the cylinder diameter (a diameter Dry of the dark band). As for the region in which the signal value is decreased, for example a half bandwidth can be used.

As shown in the present diagram, upon repeating the above-described process, when the coefficient Ay is changed via step S1414 or step S1415, the profile of the signal profile 415 is changed, and the width of the size 416 which is acquired as the diameter Dry of the dark band is also changed.

The processing order of the major-axis direction and the minor-axis direction can be reversed.

Figure 14:
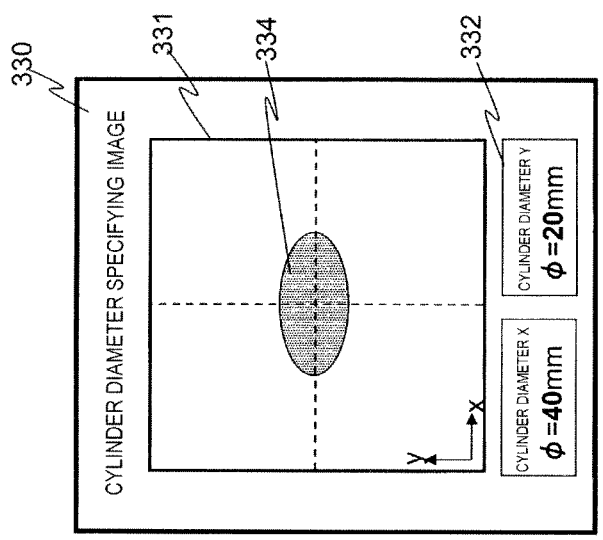
FIG. 14 is a view for explaining another example of a cylinder diameter specifying region in a specification screen of the present embodiment.

Also, an example of a cylinder diameter specifying region 330 in the specification screen 300 displayed on the display 111 of this case will be shown in FIG. 14. The cylinder diameter specifying region 330 comprises a diameter specifying region 331 and a numeric value display region 332. The diameter specifying region 331 comprises a guideline 333 for indicating the center of an irradiation region by 2DRF. In the diameter specifying region 331, a cylinder cross-section display 334 for showing the cross-sectional region of a cylinder is displayed in advance. Here, an ellipse is displayed. The operator adjusts the size of the cylinder cross-section display 334 which is displayed on the diameter specifying region 331 using a mouse, etc. provided to the operation unit 112. The diameter in the x-axis direction and the diameter in the y-axis direction of the cylinder diameter acquired as the result of the adjustment are displayed on the numeric value display region 332 by numeric values.

The cylinder diameter may also be inputted by a numeric value via the numeric value display region 332. In this case, the size of the cylinder cross-section display 334 is changed to match the cylinder diameter inputted by the operator via the numeric value display region 332, and is displayed on the diameter specifying region 331.

In the offset position adjusting process of the case that the cylinder profile is an ellipse, time differences TimeDx and TimeDy wherein the specified offset position and the actual offset position are matched are also determined with respect to the x-axis direction and the y-axis direction respectively.

Also, while the consistency of the specified offset position and the actual offset position is confirmed by generating a reference signal profile from the data without offset for comparison in the offset position adjusting process of the above-described embodiment, the method for confirming the consistency is not limited thereto. Determination can be made by only using the profiles of the acquired signal profiles 847 and 848.

In other words, when the time difference TimeD is set appropriately, the dark band region 722 coincides with the dark band region 822. Therefore, in the images 841 and 842 obtained by inverse Fourier transforming the second difference image 840, the signals 743 and 843 and the signals 744 and 844 respectively coincide with each other. Therefore, the signal profiles 847 and 848 have a profile with one peak. Accordingly, for example, when the acquired signal profiles 847 and 848 are scanned and they each have one peak, it is determined that the respective signals are matched and the excited positions thereof are coincided with each other.

Also, as another method for confirming consistency, the position of the peak can be digitalized as coordinates. Since the FOV of the second difference image 840 is already given by the imaging condition, etc., the coordinates of any point within the second difference image 840 (for example, the lower-left corner) is defined as the origin ((x,y)=(0,0)), and the position of the peak of the signal profiles 847 and 848 are digitalized respectively as the coordinates such as (x1,y1) and (x2,y2). Then if the peaks of both signal profiles 847 and 848 are overlapped and the coordinates of the peaks are matched ((x1,y1)=(x2,y2)), the excited positions are determined as consistent. In addition, in any method for confirming the consistency, as in the method for confirming the consistency in the above-described embodiment, an admissive range may also be set to determine the consistency when the value is within the range.

Second Embodiment

Next, the second embodiment to which the present invention is applied will be described.

A 2-dimensional selective excitation sequence is used for various applications such as for pre-saturation, acquisition of navigator echoes, magnetization inversion, and labeling. Various cylinder diameters need to be set for measurements in these applications.

For example, when the labeling is executed on a specified blood vessel having a diameter of several mm using a 2-dimensional selective excitation pulse, the cylinder diameter needs to be set in accordance with the diameter of the blood vessel. Also, when the sequence is used as a navigator echo, the cylinder diameter needs to be set in accordance with the region of which the breathing movement is to be monitored.

In the present embodiment, in the initial setting upon installation, etc., the optimum adjustment values (coefficient A and time difference TimeD) by which 2-dimensional selective excitation may be executed are calculated for each application, and stored as a table. Then the optimum adjustment values are selected from the table according to the application at the time of executing the 2-dimensional selective excitation sequence.

Figure 15:
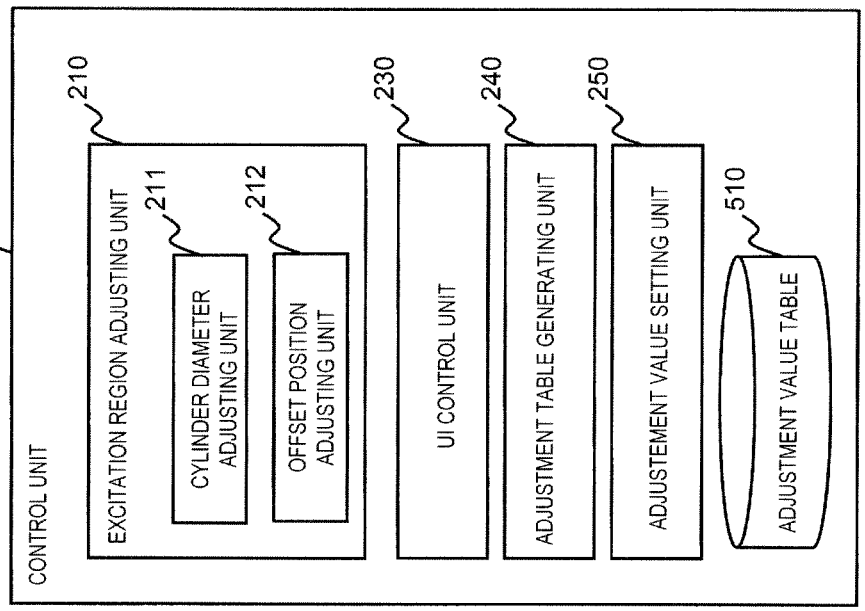
FIG. 15 is a functional block diagram showing a part related to the excitation region adjusting process in a control unit of a second embodiment.

The MRI apparatus 100 in the present embodiment is basically the same as the one in the first embodiment, except the configuration of the control unit 110. FIG. 15 is a functional block diagram of the control unit 110 in the present embodiment. As mentioned above, in the present embodiment, the cylinder diameter and the offset position are set for each application, and the coefficient A and the time difference TimeD are calculated using the method in the first embodiment. Then the calculation results are stored corresponding to the information which specifies the application. In order to execute the above-mentioned process, the control unit 110 of the present embodiment comprises an adjustment value table 510 which stores the adjustment values in its storage device. Also, the control unit 110 further comprises an adjustment value table generating unit 240 which calculates the coefficient A and the time difference Time D for each application according to the command from the operator and stores the calculated values in the adjustment value table 510, and an adjustment value setting unit 250 which extracts the coefficient A and the time difference TimeD from the adjustment value table 510 according to the command from the operator and sets the extracted values in the imaging sequence.

In the control unit 110, the CPU executes the process of the adjustment value generating unit 240 and the adjustment value setting unit 250 by loading the program which is previously stored in the storage device to a memory and executing the program.

At the time of setting the initial value upon installation of the apparatus, etc., the adjustment value generating unit 240 in the present embodiment causes the excitation region adjusting unit 210 to execute the excitation region adjusting process according to the command from the operator and to calculate the coefficient A and the time difference TimeD for each application using the same method in the first embodiment, and stores the calculated values in the adjustment value table 510.

Figure 16:
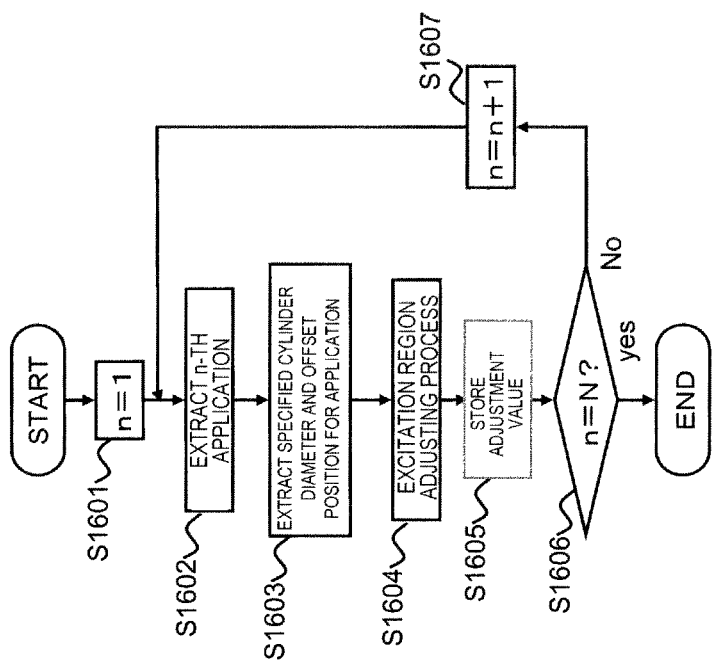
FIG. 16 is a flowchart of the adjustment value table generating process in the second embodiment.

The flow of the adjustment value generating process by the adjustment value table generating unit 240 in the present embodiment will be described referring to FIG. 16. Here, the applications to be possibly executed by the MRI apparatus 100 of the present embodiment is set as N-kinds (N=positive whole number). Here, the optimum cylinder diameter and the optimum offset position are assumed to be registered in advance in the storage device for each application. The stored values are read out in the process for each application, and are used as the specified cylinder diameter and the specified offset positions for executing the process.

A counter n for counting the kind of applications is initialized (n=1) (step S1601). Next, the n-th application is extracted from the area in which the applications are stored (step S1602). Then the specified cylinder diameter and the specified offset position of the relevant application are extracted from the area in which these values are stored (step S1603). After that, step S1102 and step S1104 of the excitation region adjusting process shown in FIG. 4 are executed (step S1604). Then the acquired adjustment values are stored in the adjustment value table 510 while being corresponded to the application (step S1605). The above-described process is executed for all applications (steps S1606 and S1607).

Here, it may also be configured so that a specification screen is displayed for each application, input of the specified cylinder diameter and the specified offset position is received, and the coefficient A and the time difference TimeD are calculated in accordance with the received values.

FIG. 17 is a view for explaining the adjustment value table 510 in the present embodiment. In the adjustment value table 510, an application information 511 which is the information for specifying the application, a coefficient A512 for making the excitation size of the 2-dimensional selective excitation sequence to be the optimum cylinder diameter for the relevant application, and a time difference TimeD613 for making the excitation position of the 2-dimensional selective excitation sequence to be the optimum offset position for the relevant application are stored while being corresponded to one another.

After the apparatus is installed and the selection of application inputted by an operator is received, the adjustment value setting unit 250 extracts the coefficient A512 and the time difference TimeD513 stored while being corresponded to the application selected by the operator (application information 511) referring to the adjustment value table 510, and the 2-dimensional selective excitation sequence 600 is generated.

Figure 18:
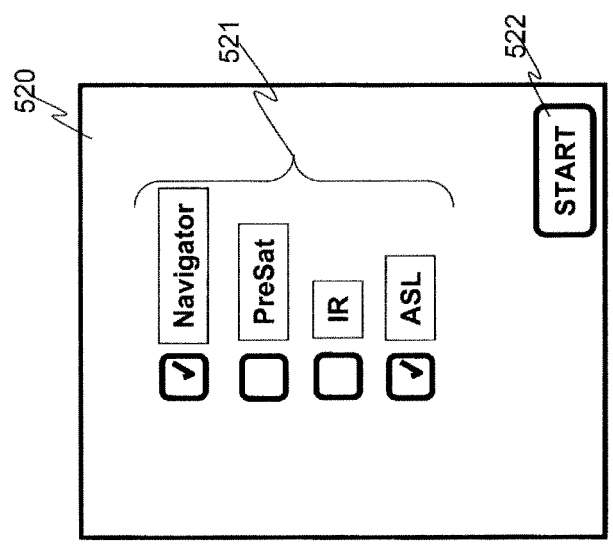
FIG. 18 is a view for explaining an example of an application inputting screen in the second embodiment.

FIG. 18 shows an example of an application input screen 520 to be displayed on the display unit 111 for the operator to select the application. As shown in the present diagram, the application input screen 520 in the present embodiment comprises an application receiving sector 521 which receives the input of the application and a start button 522 which receives the command to start execution of the sequence. The adjustment value setting unit 250 receives the information that the start button 522 is pushed down, reads the application specified in the application receiving sector 521, and carries out the above-described process.

The UI control unit 230, upon receiving the command from the operator to execute the 2-dimensional selective excitation sequence, generates the application input screen 520 from the previously stored screen data and displays the generated screen on display 111.

As described above, in accordance with the present embodiment, it is possible to automatically and accurately correct the error in the size of the cylinder excitation region attributed to the characteristic of each device for each application. Accordingly, a 2-dimensional selective excitation sequence can be executed using the optimum cylinder diameter and the offset position for each application. Thus, the effect of 2DRF pulses can be provided with high accuracy without subjecting an object to additional burden, which leads to acquisition of high quality images.

Also in accordance with the present embodiment, since calculation of the optimum adjustment values is not performed upon imaging, the time for executing imaging sequence will not be prolonged.

In the present embodiment, the MRI apparatus 100 does not have to comprise the excitation region adjusting unit 210 and the adjustment value table generating unit 240. For example, an information processing device which is independent from the MRI apparatus 100 and is capable of communicating with the MRI apparatus 100 comprises the excitation region adjusting unit 210 and the adjustment value table generating unit 240, and the adjustment value table generating unit 240 creates the adjustment value table 510 on the relevant information processing device before the apparatus's shipment and stores the generated table in a storage unit in the control unit 110.

While it is configured that the adjustment value table 510 stores adjustment values for each application, the configuration is not limited thereto. The adjustment values may also be stored for each combination of the cylinder diameter and the offset position. The adjustment value setting unit 250 extracts the corresponding adjustment value from the adjustment value table 510 in accordance with the optimum cylinder diameter and offset position for each application.

Figure 19:
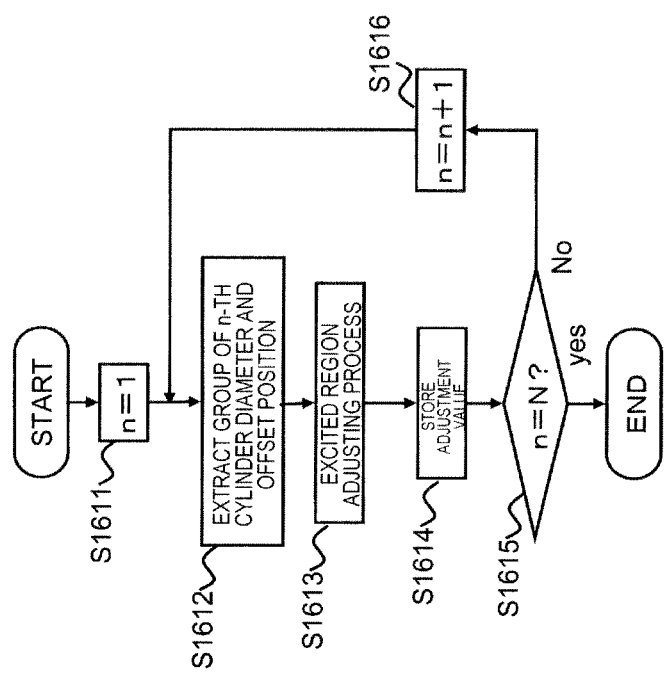
FIG. 19 is a flowchart of another example of the adjustment value table generating process in the second embodiment.

The flow of the adjustment value table generating process by the adjustment value table generating unit 240 in this case will be described referring to FIG. 19. Here, it is assumed that there are N-kinds of possible combinations of the cylinder diameter and the offset position to be executed by the MRI apparatus 100 in the present embodiment (N is a positive whole number).

A counter n for counting the kind of combination of the cylinder diameter and the offset position is initialized (n=1) (step S1611). Next, the n-th combination is extracted from the stored area (step S1612). Then step S1102 and step S1104 of the excitation region adjusting process shown in FIG. 4 are executed (step S1613). And the acquired adjustment values are stored in the adjustment value table 510 while being corresponded to the combination of the cylinder diameter and the offset position (step S1614). The above-described process is executed in all combinations (steps S1615 and S1616).

In the 2-dimensional selective excitation sequence, there are cases that the approximately same size of cylinder diameter may be used for different applications. By storing the adjustment values (coefficient A and time difference TimeD) according to the cylinder size in place of the application, overlapping of stored data can be avoided in such a case.

Third Embodiment

Next, the third embodiment to which the present invention is applied will be described. In the above-described respective embodiments, adjustment is made as the initial setting at the time of installing an apparatus, etc. However in the present embodiment, necessity of adjustment is determined for each imaging, and the excitation region adjusting process is executed if necessary. The present embodiment will be described below.

Figure 20:
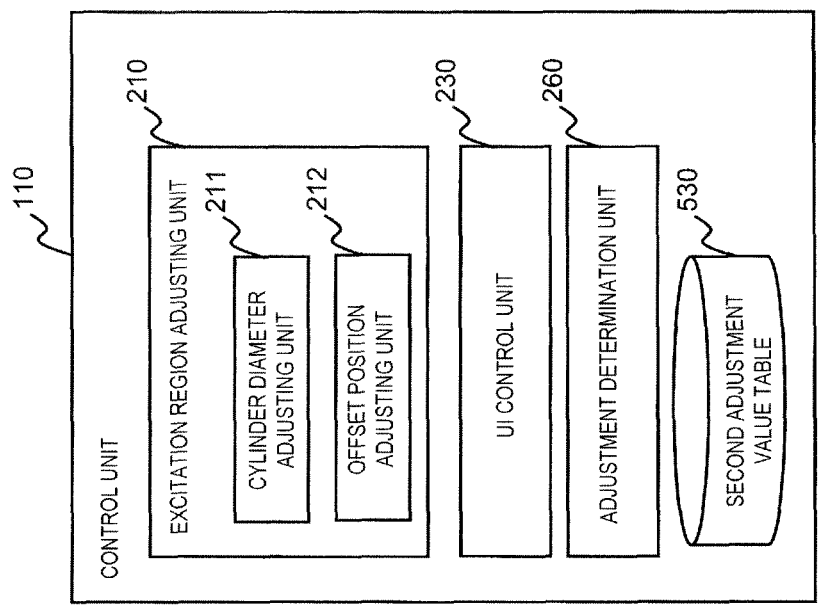
FIG. 20 is a functional block diagram showing a part related to the excitation region adjusting process by a control unit in a third embodiment.

The configuration of the MRI apparatus 100 in the present embodiment is basically the same as the first embodiment, except the configuration of the control unit 110. FIG. 20 is a functional block diagram of the control unit 110 in the present embodiment. The control unit 110 in the present embodiment comprises an adjustment determination unit 260 which determines the necessity of adjustment. Also, the control unit 111 in the present embodiment comprises a second adjustment value table 530 in a storage device thereof for determining the necessity of adjustment.

In the present embodiment, when imaging is executed using the 2-dimensional selective excitation sequence at the same time, in prior to the execution of the 2-dimensional selective excitation sequence, the excitation region adjusting process is executed in accordance with the cylinder diameter required in the relevant 2-dimensional selective excitation sequence, so as to determine the adjustment values (coefficient A and time difference TimeD).

FIG. 21 is a view for explaining the second adjustment value table 530. As shown in the present diagram, the adjustment value table 530 comprises a cylinder size storing unit 535 which stores the combination of a cylinder diameter 531 and an offset position 532, and an adjustment value storing unit 536 which stores the combination of a coefficient A533 and a time difference TimeD that are the adjustment values in accordance with the cylinder size stored in the cylinder size storing unit 535.

Also, the adjustment determination unit 260 of the present embodiment, when receiving the input of the cylinder diameter and the offset position upon imaging, determines whether or not the combination of the cylinder diameter and the offset position is stored in the cylinder size storing unit 535 of the adjustment value table 530. The control unit 110 causes the excitation region adjusting unit 210 to execute the excitation region adjusting process according to the determination result, and stores the result in the adjustment value table 530.

Figure 22:
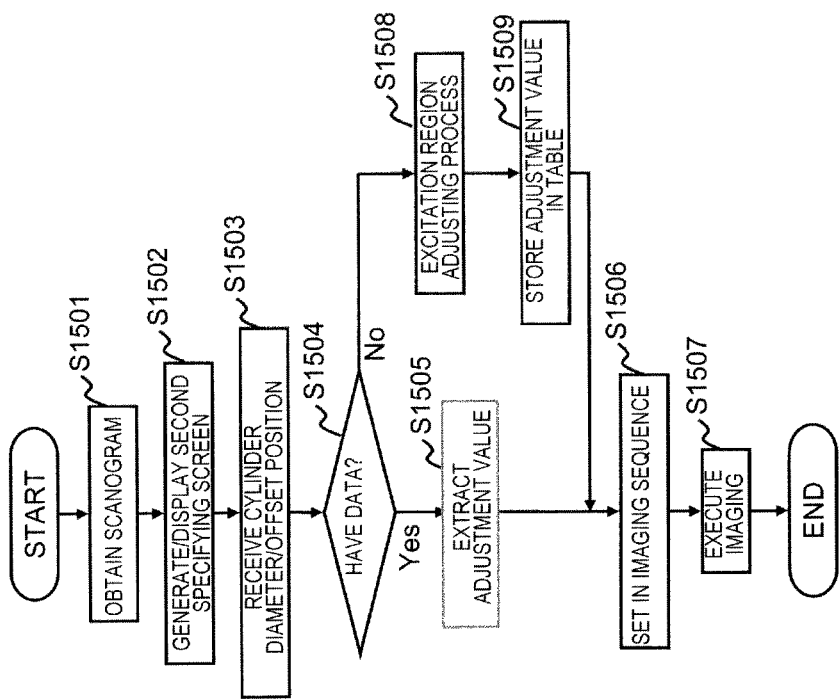
FIG. 22 is a flowchart of the imaging process by a control unit in the third embodiment.

The flow of the process upon imaging by the control unit 110 in the present embodiment will be described below including the process of the adjustment determination unit 260. The processing flow in this case is shown in FIG. 22.

When the command to start imaging is received, the control unit 110 executes scanogram imaging for obtaining a positioning image (scanogram image) (step S1501). The scanogram image is obtained according to the application of imaging. For example, if the purpose is to use as a navigator echo, an image of the region in which the navigator application position (diaphragm or abdominal wall) and an imaging target region can be viewed is obtained.

Figure 23:
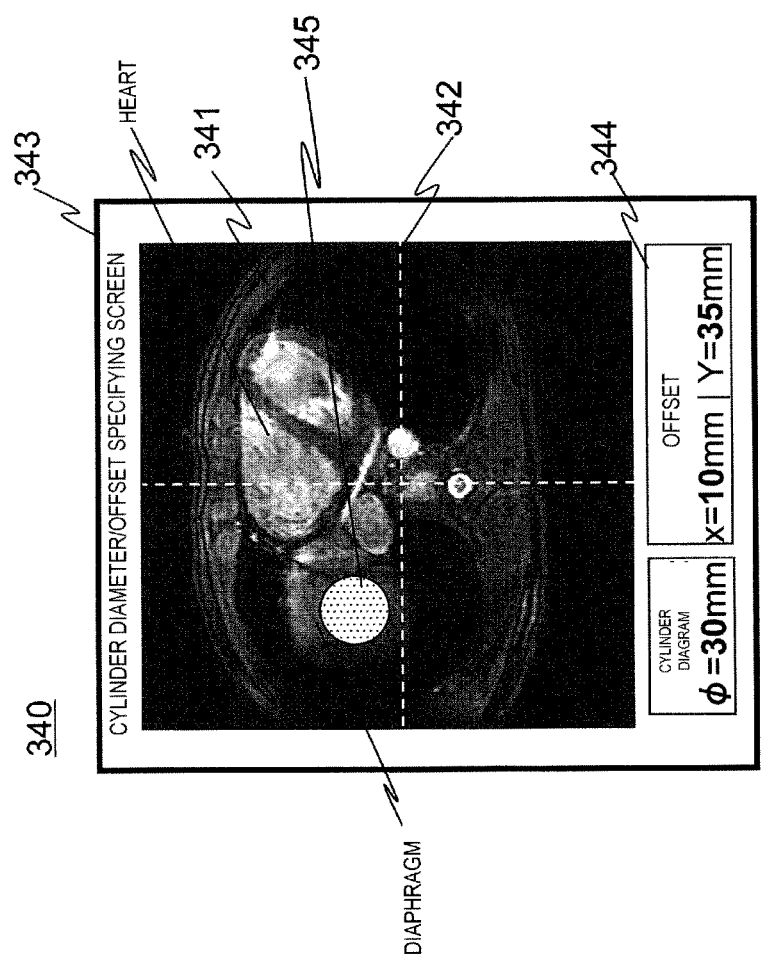
FIG. 23 is a view for explaining a second specification screen in the third embodiment.

The UI control unit 230 generates a second specification screen 340 using the scanogram, and displays it on the display unit 111 (step S1502). An example of the specification screen 340 using a scanogram is shown in FIG. 23. On the specification screen 340, a scanogram image 341 and a guideline 342 are displayed, and a specification receiving image region 343 which receives the specification of the cylinder diameter and the offset position and a numeric value display region 344 which displays the cylinder diameter and the offset position 343 received in the specification receiving image region 343 by numeric values are provided therein.

The guideline 342 indicates the center of an irradiation region by 2DRF. The operator adjusts the diameter and the offset position of a cylinder cross-section display 345 in the specification receiving image region 343 using a mouse, etc. provided to the operation unit 111, and inputs desired cylinder diameter and the offset position. It may also be configured to receive the input of a numeric value via the numeric display region 344 and display the result on the specification receiving image region 343 as in the first embodiment.

When input of the cylinder diameter and the offset position are received via the second specification screen 340 (step S1503), the control unit 110 causes the adjustment determination unit 260 to determine whether or not the excitation region adjusting process is already performed and the adjustment values are stored regarding the received cylinder diameter and the offset position (step S1504). The adjustment determination unit 260 refers to the second adjustment value table 530 and determines if the values are stored or not. Then the determination is made as already processed if the values are stored, and the determination is made as not processed if the values are not stored.

In step S1504, in the case that the determination is made as already processed, the control unit 110 extracts the coefficient A and the time difference TimeD stored in the second adjustment value table 530 by corresponding them to the received combination of the cylinder diameter and the offset position (step S1505). Then the extracted adjustment values are applied to the 2-dimensional selective excitation sequence (step S1506), the imaging is executed (step S1507), and the process is completed.

On the other hand, when the determination is made as not processed in step S1504, the control unit 110 causes the excitation region adjusting unit 210 to execute the excitation region adjusting process using the received cylinder diameter and the offset position as the specified cylinder diameter and the offset position (step S1508). Then the acquired adjustment values (coefficient A and time difference TimeD) are stored in the second adjustment value table 530 while being corresponded to the received cylinder diameter and the offset position (step S1509). The step S1506 is carried out and the imaging is executed.

As described above, in accordance with the present embodiment, an error of the size of a cylinder excitation region generated due to the characteristic of each apparatus can be automatically and accurately corrected for each application. Accordingly, in a 2-dimensional selective excitation sequence, a desired region can be accurately excited for each application. Thus the effect of a 2DRF pulse can be accurately given without subjecting an object to additional burden, which leads to acquisition of high quality images.

Also in accordance with the present embodiment, calculation of adjustment values in advance considering all possibilities is not necessary, whereby the procedure for initial adjustment can be reduced. Also, the optimum adjustment values are calculated only one time in accordance with each of the cylinder diameters and the offset positions, which can withhold the extension of imaging sequence time compared to the configuration which calculates the values for every application.

While it is configured in the above-described embodiment so that the excitation region adjusting process is not executed for the cylinder excitation region having the same cylinder diameter and the offset position, the configuration is not limited thereto. For example, the second adjusting value table 530 may be configured to store the adjustment values corresponding to the application information similarly as the adjustment value table 510 in the second embodiment, and to calculate the adjustment values one time for each application.

Since the calculation is executed only one time per application, extension of imaging sequence time can be withheld compared to the configuration which executes the calculation for each imaging.

Also, it may be configured to surely execute the excitation region adjusting process for each imaging. In this manner, the inconsistency due to inhomogeneity of the static magnetic field, etc. can also be adjusted, which increases the accuracy in adjustment.

While the case in which both the cylinder diameter and the offset position are adjusted in a cylinder excitation region by the 2-dimensional selective excitation sequence is exemplified in the above-described respective embodiments, it may also be configured to perform the adjustment process on only one of them.

DESCRIPTION OF REFERENCE NUMERALS

100: MRI apparatus
101: object
102: magnet
103: gradient magnetic field coil
104: RF coil
105: RF probe
106: gradient magnetic field power source
107: RF transmission unit
108: signal detection unit
109: signal processing unit
110: control unit
111: display unit
112: operation unit
113: bed
210: excitation region adjusting unit
211: cylinder diameter adjusting unit
212: offset position adjusting unit
230: UI control unit
240: adjustment value table generating unit
250: adjustment value setting unit
260: adjustment determination unit
300: specification screen
310: cylinder diameter specifying region
311: diameter specifying region
312: numeric value display region
313: guideline
314: cylinder cross-section display
320: offset position specifying region
321: position specifying region
322: numeric value display region
323: guideline
324: cylinder cross-section display
330: cylinder diameter specifying region
331: diameter specifying region
332: numeric value display region
333: guideline
334: cylinder cross-section display
340: second specification screen
341: scanogram image 342: guideline
343: specification receiving image region
344: numeric value display region
401: phantom image
402: dark band
403: line
404: signal profile
405: half bandwidth
411: phantom image
412: dark band
413: line
414: signal profile
415: half bandwidth
421: phantom image
422: dark band
423: line
424: signal profile
510: adjustment value table
511: application information
512: coefficient
513: time difference
520: application input screen
521: application receiving region
522: start button
530: second adjustment value table
531: cylinder diameter
532: offset position
533: coefficient
534: time difference
535: cylinder size storing unit
536: adjustment value storing unit
600: 2-dimensional selective excitation sequence
611: 2DRF pulse
612: oscillating gradient magnetic field
613: oscillating gradient magnetic field
710: template image
711: image
712: region
720: template image
722: dark band region
743: signal
744: signal
810: first image
812: dark band region
820: second image
830: first difference image
831: image
832: image
833: image
834: image
835: line
836: line
837: signal profile
838: signal profile
840: second difference image
841: image
842: image
843: signal
844: signal
845: line
846: line
847: signal profile
848: signal profile
901: signal profile
902: signal profile
903: signal profile

The invention claimed is:

1. A magnetic resonance imaging apparatus which collects echo signals generated by applying a high-frequency magnetic field and a gradient magnetic field to an object to be examined, which has been placed in a static magnetic field, in accordance with a predetermined pulse sequence and reconstructs an image from the collected echo signals, comprising:
   an adjustment unit configured to adjust a profile of an excitation region to be excited by a local excitation sequence, the adjustment unit using (a) a profile adjustment value of the local excitation sequence and (b) a profile adjustment value table in which profile parameters associated with corresponding adjustment values of the local excitation sequence for exciting the excitation region to obtain a specific profile are stored,
   a profile adjustment value calculating unit configured to calculate the profile adjustment value of the local excitation sequence, for exciting the excitation region to have an excitation region profile specified by an operator, and
   a determination unit configured to determine whether or not a corresponding adjustment value associated with a combination of the profile parameters corresponding to the excitation region profile specified by the operator is stored in the profile adjustment value table,
   wherein the profile adjustment value calculating unit calculates the profile adjustment value of the local excitation sequence when the determination unit determines that the corresponding adjustment value associated with the profile parameters corresponding to the excitation region profile specified by the operator is not stored in the profile adjustment value table.

2. The magnetic resonance imaging apparatus according to claim 1, wherein the profile is adjusted by setting the profile adjustment value calculated by the profile adjustment value calculating unit to the local excitation sequence.

3. The magnetic resonance imaging apparatus according to claim 1, wherein the adjustment unit comprises a positional adjustment value calculating unit configured to calculate a positional adjustment value of the local excitation sequence for exciting the position of the excitation region based on the excitation region set by an operator, and the position is adjusted by setting the positional adjustment value calculated by the positional adjustment value calculating unit to the local excitation sequence.

4. The magnetic resonance imaging apparatus according to claim 1, wherein the adjustment unit comprises:
   a profile adjustment value table generating unit configured to generate the profile adjustment value table; and
   a profile adjustment value extracting unit configured to extract from the profile adjustment value table, at the time of imaging, the profile adjustment values which are stored for each application and correspond to the optimum profile for implementing the relevant application,
   wherein the adjustment unit adjusts the profile by setting the extracted profile adjustment values to the local excitation sequence.

5. The magnetic resonance imaging apparatus according to claim 4, further comprising a profile adjustment value table generating unit configured to store the profile adjustment value calculated by the profile adjustment value calculating unit to the profile adjustment value table.

6. A magnetic resonance imaging apparatus which collects echo signals generated by applying a high-frequency magnetic field and a gradient magnetic field to an object to be examined, which has been placed in a static magnetic field, in accordance with a predetermined pulse sequence and reconstructs an image from the collected echo signals, comprising:

an adjustment unit configured to adjust a position of an excitation region to be excited by a local excitation sequence, the adjustment unit using (a) a positional adjustment value of the local excitation sequence and (b) a positional adjustment value table in which positional parameters associated with corresponding adjustment values of the local excitation sequence for exciting the excitation region at a specific position are stored;

a positional adjustment value calculating unit configured to calculate the positional adjustment value of the local excitation sequence for exciting the excitation region at an excitation region position specified by an operator, and a determination unit configured to determine whether or not a corresponding adjustment value associated with a combination of the positional parameters corresponding to the excitation region position specified by the operator is stored in the positional adjustment value table, wherein the positional adjustment value calculating unit calculates the positional adjustment value of the local excitation sequence, when the determination unit determines that the corresponding, adjustment value associated with the positional parameters corresponding to the excitation region position specified by the operator is not stored in the positional adjustment value table.

7. The magnetic resonance imaging apparatus according to claim 6, further comprising:

a positional adjustment value table generating unit configured to store the positional adjustment value calculated by the positional adjustment value calculating unit to the positional adjustment value table.

8. The magnetic resonance imaging apparatus according to claim 2, wherein the profile adjustment value includes a coefficient which is related to an amplitude of a gradient magnetic field.

9. The magnetic resonance imaging apparatus according to claim 3, wherein the positional adjustment value includes a time difference between an application starting time of a high-frequency magnetic field and an application starting time of a gradient magnetic field.

10. The magnetic resonance imaging apparatus according to claim 1, wherein:

the local excitation sequence is a 2-dimensional selective excitation sequence; and the excitation region is a cylinder-shaped region.

11. An excitation region adjusting method for adjusting an excitation region to be obtained by executing a local excitation sequence by a magnetic resonance imaging apparatus having a profile adjustment value table in which profile parameters associated with corresponding adjustment values of the local excitation sequence for exciting the excitation region to obtain a specific profile are stored, including:

a determination step of determining whether or not a corresponding adjustment value associated with a combination of the profile parameters corresponding to an excitation region profile specified by an operator is stored in the profile adjustment value table;

a profile adjustment value calculating step of calculating a profile adjustment value of the local excitation sequence for exciting the excitation region to obtain the excitation region profile specified by the operator, when the determination step determines that the corresponding adjustment value associated with the profile parameters corresponding to the excitation region profile specified by the operator is not stored in the profile adjustment value table; and a profile adjustment value setting step of setting the profile adjustment value calculated by the profile adjustment value calculating step to the local excitation sequence.

12. An excitation region adjusting method for adjusting an excitation region to be obtained by executing a local excitation sequence by a magnetic resonance imaging apparatus having a positional adjustment value table in which positional parameters associated with corresponding adjustment values of the local excitation sequence for exciting the excitation region at a specific position are stored, including:

a determination step of determining whether or not a corresponding adjustment value associated with a combination of the positional parameters corresponding to an excitation region position specified by an operator is stored in the positional adjustment value table, a positional adjustment value calculating step of calculating a positional adjustment value of the local excitation sequence for exciting the excitation region at the excitation region position specified by the operator, when the determination step determines that the corresponding adjustment value associated with the positional parameters corresponding to the excitation region position specified by the operator is not stored in the positional adjustment value table; and a positional adjustment value setting step of setting the positional adjustment value calculated by the positional adjustment value calculating step to the local excitation sequence.

13. The magnetic resonance imaging apparatus according to claim 1, wherein the profile of the excitation region to be excited by the local excitation sequence includes a cylinder diameter and an offset position of the excitation region specified by the operator.

* * * * *